(12) United States Patent
Schuler et al.

(10) Patent No.: US 8,574,901 B2
(45) Date of Patent: Nov. 5, 2013

(54) CRYOCONSERVED MATURE DENDRITIC CELLS

(75) Inventors: Gerold Schuler, Spardorf (DE); Beatrice Schuler-Thurner, Spardorf (DE)

(73) Assignee: Argos Therapeutics, Inc., Durham, NC (US)

( * ) Notice: Subject to any disclaimer, the term of this patent is extended or adjusted under 35 U.S.C. 154(b) by 0 days.

(21) Appl. No.: 13/479,612

(22) Filed: May 24, 2012

(65) Prior Publication Data

US 2012/0301959 A1 Nov. 29, 2012

Related U.S. Application Data

(62) Division of application No. 10/362,715, filed as application No. PCT/EP01/09790 on Aug. 24, 2001, now Pat. No. 8,236,562.

(30) Foreign Application Priority Data

Aug. 24, 2000 (DE) .................................. 100 41 515

(51) Int. Cl.
C12N 5/071 (2010.01)
C12N 5/00 (2006.01)
C12N 5/02 (2006.01)

(52) U.S. Cl.
USPC .......................................... 435/372; 435/374

(58) Field of Classification Search
None
See application file for complete search history.

(56) References Cited

U.S. PATENT DOCUMENTS

| 5,308,626 A | 5/1994 | Landucci et al. |
| 5,759,764 A | 6/1998 | Polovina |
| 5,788,963 A | 8/1998 | Murphy et al. |
| 6,248,588 B1 | 6/2001 | Crespo et al. |
| 6,548,297 B1 | 4/2003 | Kuri-Harcuch et al. |

FOREIGN PATENT DOCUMENTS

| EP | 0922758 A2 | 6/1999 |
| JP | 10-323944 | 5/2000 |
| WO | 9613158 A2 | 5/1996 |
| WO | 9614738 A2 | 5/1996 |
| WO | 9704802 A1 | 2/1997 |
| WO | 9900137 A3 | 1/1999 |
| WO | 9946984 A1 | 9/1999 |

OTHER PUBLICATIONS

Wikipedia, "Daunorubicin," http://en.wikipedia.org/wiki/Daunomycin, printed Feb. 13, 2005.
Woolley et al., "Mast cell activation and its relation to primflammatory cytokine production in the rheumatoid lesion", Arthritis Res., 2000, pp. 65-74, vol. 2.
Boczkowski et al., "Dendritic cells pulsed with RNA are potent antigen-presenting cells in vitro and in vivo", J. Exp. Med., 1996, pp. 455-472, vol. 184.
Bjorck et al., "CD40 ligation counteracts Fas-induced apoptosis of human dendritic cells," Int. Immunol., 1997, pp. 365-372, vol. 9.
Caux et al., "CD34 Hematopoietic progenitors from human cord blood differentiate along two independent dendritic cell pathways in response to GM-CSF + TF-α", J. Exp. Med., 1996, pp. 695-706, vol. 184.
De Boer et al., "Changes in L-selectin expression on CD34-positive cells upon cryopreservation of peripheral blood stem cell transplants", Bone Marrow Transplantation, 1998, pp. 1103-1110, vol. 22.
Fanger et al., "Characterization of expression, cytokine regulation, and effector function of the high affinity IgG receptor Fc[gamma]R1 (CD64) expressed on human blood dendritic cells," J. Immunol., 1997, pp. 3090-3098, vol. 158.
Feuerstein et al., "A method for the production of cryopreserved aliquots of antigen-preloaded, mature dendritic cells ready for clinical use", J. Immunol. Meth., 2000, pp. 15-29, vol. 245.
Fujii et al., "Presentation of tumor antigens by phagocytic dendritic cell clusters generated from human CD34+ hematopoietic progenitor cells . . . ," Cancer Res., 1999, pp. 2150-2158, vol. 59.
Horckmans et al., "Extracellular adenine nucleotides inhibit the release of major monocyte recruiters by human monocyte-derived dendritic cells," FEBS Letter, 2006, pp. 747-754, vol. 580.
Invitrogen, "Media formulations," printed Feb. 7, 2006, http://www.invitrogen.com/content.cfm? pageld=95&fuseaction=MediaForm.dsp_mediaForm . . . , pp. 1-3.
Jonuleit et al., "Pro-inflammatory cytokines and prostaglandins induce maturation of potent immunostimulatory dendritic cells under fetal calf serum-free conditions," Eur. J. Immunol., 1997, pp. 3135-3142, vol. 27.
Lewalle et al., "Freezing of dendritic cells, generated from cryopreserved leukaphereses, does not influence their ability to induce antigen-specific immune responses or functionally react to maturation stimuli", J. Immunol. Meth., 2000, pp. 69-78, vol. 240.
Liu et al., "Transfected human dendritic cells as cancer vaccines", Nat. Biotech, 1998, pp. 335-336, vol. 18. Makino et al., "A cryopreservation method of human peripheral blood mononuclear cells for efficient production of dendritic cells", Scand. J. Immunol., 1997, pp. 618-622, vol. 45.

(Continued)

*Primary Examiner* — Amy Juedes
(74) *Attorney, Agent, or Firm* — Elaine T. Sale; Leigh W. Thorne

(57) ABSTRACT

The invention relates to a method for producing ready to use, antigen loaded or unloaded, cryoconserved mature dendritic cells especially for the production of a vaccine containing said dendritic cells, wherein immature dendritic cells are cultivated in the presence of suitable maturation stimuli and the mature dendritic cells thus obtained are frozen. The dendritic cells can be loaded with antigen before freezing. The invention also relates to a vaccine which can be obtained according to the inventive method and to a composition containing frozen, mature dendritic cells which are loaded with antigen.

10 Claims, 36 Drawing Sheets

(56) References Cited

OTHER PUBLICATIONS

Popov et al., "Techniques for long-term storage of human lymphocytes," Bulletin of Exp. Biol. and Med., 1976, pp. 949-951, vol. 81.

Reis E Sousa, "Toll-like receptors and dendritic cells: for whom the bug tolls," Seminars in Immunology, 2004, pp. 27-34, vol. 16.

Romani et al., "Generation of mature dendritic cells from human blood: An improved method with special regard to clinical applicability", J. Immunol. Meth., 1996, pp. 137-151, vol. 196.

Sato et al., "Generation of dendritic cells from fresh and frozen cord blood CD34+ cells", Cryobiology, 1998, pp. 362-371, vol. 37.

Stroncek et al., "Retroviral transduction and expansion of peripheral blood lymphocytes for the treatment of mucopolysaccharidosis type II, Hunter's Syndrome", Transfusion, 1999, pp. 343-350, vol. 39.

Taylor et al., "The cryobiology of rat and human dendritic cells: preservation and destruction of membrane integrity by freezing", Cryobiology, 1990, pp. 269-278, vol. 27.

Thurner et al., "Generation of large numbers of fully mature and stable dendritic cells from leukapheresis products for clinical application", J. Immunol. Meth., 1999, pp. 1-15, vol. 223.

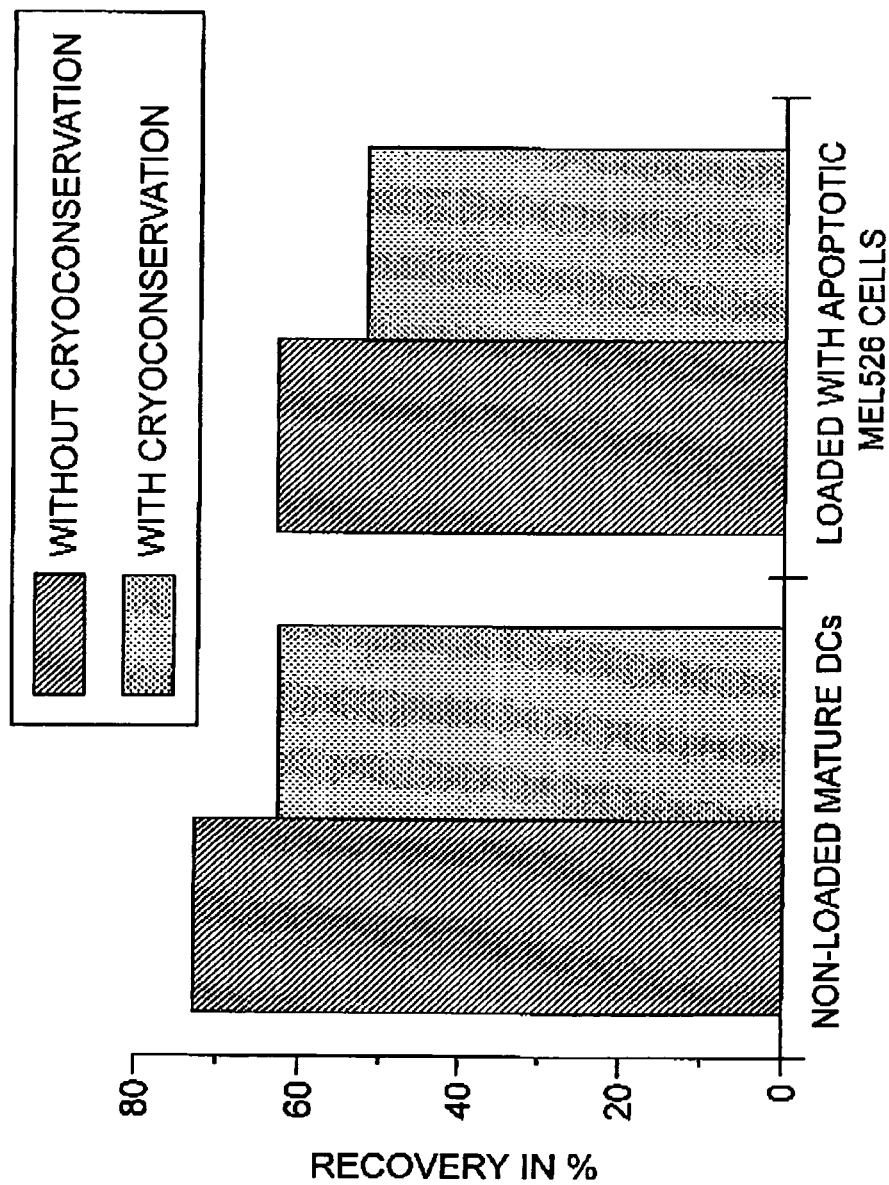

| PEPTIDE DESIGNATION | HLA RESTRICTION | SEQUENCE | SEQ ID NO: | REFERENCE |
|---|---|---|---|---|
| | A1 (48%) | | | |
| INFLUENZA MATRIX | A2.1 | GILGFVFTL | 1 | J. EXP. MED. 186:859 (1997) |
| INFLUENZA B NP AS 85-94 | A2.1 | KLGEFYNQMM | 3 | IMMUNOGENETICS 41:78 (1995) |
| MAGE-3A2 | A2.1 | FLWGPRALV | 4 | EUR. J. IMMUNOL. 24:3038 (1994) |
| MART 1/MELAN A, AS 26-35 ANA* | A2.1 | ELAGIGILTV | 2 | J. IMMUNOL. 160:1750 (1998) |
| GP 100, AS 209-217 ANA* | A2.1 | IMDQVPFSV | 5 | NATURE MEDICINE 3:321 (1998), J. IMMUNOL. 157:2539 (1996) |
| TYROSINASE AS 368-376 | A2.1 | YMDGTMSQV | 6 | J. EXP. MED. 183:527 (1996) |
| GNTV NT 38-64 | A2.1 | VLPDVFIRCV | 7 | J EXP MED 183:1173 (1996) |
| MAGE-A10 AS 254-262 | A2.1 | GLYDGMEHL | 8 | J. IMMUNOL. 162:6849 (1999) |
| MAGE-A4 AS 230-239 | A2.1 | GVYDGREHTV | 9 | EUR. J. IMMUNOL. 29:3329 (1999) |
| | A1 (26%) | | | |
| INFLUENZA NP | A1 | CTELKLSDY | 10 | J. IMMUNOL. 151:5930 (1993) |
| INFLUENZA PB1 AS 591-599 | A1 | VSDGGPNLY | 11 | J. EXP. MED. 186:859 (1997) |
| MAGE-3A1 | A1 | EVDPIGHLY | 12 | J EXP MED. 179:92 (1999) |
| MAGE-1 | A1 | EADPTGHSY | 13 | J. EXP. MED. 176:1453 (1992), INT. J. CANCER 67:54 (1996) |
| TYROSINASE AS 243-251 ANA* | A1 | KSDICTDEY | 14 | J. IMMUNOL. 160:2099 (1998) |
| | A3 (32%) | | | |
| INFLUENZA NP AS 265-273 | A3 | ILRGSVAHK | 15 | J. EXP. MED. 186:859 (1997) |
| MAGE-1 AS 96-104 | A3 | SLFRAVITK | 16 | J. IMMUNOL. 163:2928 (1999) |
| GP100 | A3 | LIYRRRLMK | 17 | J. IMMUNOL. 161:6985 (1998) |
| | A24 (18%) | | | |
| TYROSINASE | A24 | AFLPWHRLF | 18 | J. IMMUNOL. 155:155 (1995) |
| MAGE-1 | A24 | NYKHCFPEI | 19 | INT. J. CANCER 80:169 (1999) |
| GP 100 | A24 | VYFFLPDHL | 20 | J. IMMUNOL. 159:303 (1997) |
| MAGE 3 | A24 | IMPKAGLLI | 21 | CANCER RES. 57:4465 (1997) |
| | B44 (13%) | | | |
| TYROSINASE | B44 | SEIWRDIDF | 22 | EUR. J. IMMUNOL. 26:224 (1996) |
| MAGE 3 | B44 | MEVDPIGHLY | 23 | IMMUNOGENETICS 43:377 (1993) |

FIG. 28

| PEPTIDE DESIGNATION | HLA RESTRICTION | SEQUENCE | SEQ ID NO: | REFERENCE |
|---|---|---|---|---|
| TYROSINASE AS 450-462 ANA* | DRB1*0401[b] [20-25%] | SYLQDSVPDSFQD | 24 | J. EXP. MED. 183:1965 (1996) |
| GP100 | DRB1*0401[b] [20-25%] | WNRQLYPEWTEAQRLD | 25 | CANCER IMMUNOL. IMMUNOTHER. 147:32 (1998) |
| MAGE-3 AS 121-134 | DRB1*1301 DRB1*1302 [20-25%][c] | LLKYRAREPVTKAE | 26 | J. EXP. MED. 189:767-778 (1999) |
| MAGE-3 AS 243-258 | DPB1*0401 [64%] DPB1*0402[d] [21%] | KKLLTQHFVQENYLEY | 27 | UNPUBLISHED; T. BOON, PERSONAL COMMUNICATION |

FIG. 28 (CONTINUED)

CRYOCONSERVED MATURE DENDRITIC CELLS

TECHNICAL FIELD

The present invention relates to a method for the preparation of ready-for-use cryoconserved mature dendritic cells, especially for the preparation of a vaccine which contains such dendritic cells, wherein immature dendritic cells are cultured in the presence of suitable maturing stimulants, and the mature dendritic cells thus obtained are frozen. Prior to or after freezing, the dendritic cells may be loaded with antigen. The invention also relates to a vaccine obtainable by the method according to the invention, and to a composition containing frozen mature antigen-loaded dendritic cells.

BACKGROUND OF THE INVENTION

Dendritic cells (hereinafter briefly referred to as "DC") are antigen-presenting cells which influence the immune system by interacting with lymphocytes. Most DCs exhibit an immunostimulatory activity. These classical DCs can induce the formation of helper and killer T cells in vivo in different ways ("nature's adjuvant"). In particular, immature DCs which occur in peripheral tissues have the capability of binding antigens and preparing immunogenic MHC peptide complexes therefrom ("antigen processing mode"). Upon the action of maturation-inducing stimulants, such as inflammatory cytokines, these immature DCs develop into potent T-cell stimulants through an increased formation of adhesion and costimulatory molecules ("T-cell stimulatory mode"). At the same time, the cells migrate into secondary lymphatic organs to select and stimulate rare antigen-specific T cells. It could be shown that DCs which were isolated from tissues or blood and loaded with antigen in vitro were immunogenic after back injection as mature DCs in vivo.

Recently, it could be shown that DCs can induce CD4+ and CD8+ T-cell immunity in both healthy humans and cancer patients. In immunocompetent healthy subjects, a single booster injection with mature DCs could enhance not only the frequency, but also the functional avidity of the CD8+ T-cell response. For these reasons, DCs (especially mature ones) are currently extremely promising adjuvants for induce potent T-cell responses against tumors and infections in humans.

One precondition for the use of DCs in immunotherapy is the development of techniques which allow to produce a great number of DCs in culture, either from proliferating CD34+ precursor cells or from non-proliferating or little proliferating CD14+ monocytic precursor cells. DCs derived from monocytes are frequently used currently because they are easily prepared without any cytokine pretreatment of the donor, and because the resulting DC population is fairly homogeneous and best characterized. For example, immature DCs can be prepared from adherent monocytes in the absence of fetal calf serum (FCS) during a culture for usually six to seven days in (GM-CSF+IL-4), followed by maturation for mostly one to three days, induced by autologous monocyte-conditioned medium. To provide an effective cryoconservation for dendritic cells or their precursor cells has proven extremely difficult, except in the presence of FCS (Taylor et al. (1990) *Cryobiology* 27, 269; Makino et al. (1997) *Scand. J. Immunol.* 45, 618). However, since FCS must not be present in vaccinations, it has still been necessary to prepare DCs freshly for each DC vaccination, either from fresh blood, from fresh leucapheresis products or from frozen PBMC ("peripheral blood mononuclear cells") aliquots from leucapheresis products (Thurner et al. (1999) *J. Immunol. Methods* 223, 1). Frozen PBMCs also have the disadvantage that following the thawing the cells must first be cultured for several days to differentiate them into DCs. Lewalle et al. (2000) *J. Immunol. Methods* 240, 69-78, disclose a method for the freezing of immature DCs, but only obtain poor yields of surviving cells (p. 71, top of left column). The freezing of immature dendritic cells prepared from monocytes by means of GM-CSF and IL-4 has also been disclosed in WO 99/46984.

SUMMARY OF THE INVENTION

Therefore, one object of the present invention is to provide a composition, such as a vaccine, which contains mature DCs, that can be stored for extended periods of time without a substantial loss in activity, and that can be administered within a short time when needed.

The DCs employed according to the invention are preferably derived from the same patient who is treated with the vaccine (autologous). Alternatively, the DCs may also be derived from other patients (allogenic), for example, from leucapheresates from normal volunteers, as described, for example, in Thurner et al. (1999) *J. Immunol. Methods* 283, 1-15.

Surprisingly, it has been found that only fully matured DCs (hereinafter also briefly referred to as "mature DCs"), which are obtainable by culturing in the presence of a suitable "maturing cocktail" with specific maturing stimulants, will survive to a high percentage after freezing without FCS and thawing, and have immunostimulant activities which are comparable to those of freshly prepared mature DCs. During the culturing with the maturing cocktail, the immature DCs are differentiated into mature DCs. A particularly preferred maturing cocktail contains interleukin-1β (IL-1β), interleukin-6 (IL-6), prostaglandin $E_2$ ($PGE_2$) and "tumor necrosis factor α" (TNFα).

Thus, the present invention relates to (1) a method for the preparation of ready-for-use cryoconserved mature dendritic cells, comprising
  a) providing immature dendritic cells (DC);
  b) culturing the immature DCs in a culture medium containing a maturing cocktail with one or more maturing stimulants to obtain mature DCs;
  c) freezing the mature DCs in a freezing medium which does not contain any heterologous serum;

(2) a method as defined above under (1) which is suitable for the preparation of a vaccine from mature cryoconserved DCs;

(3) frozen mature antigen-loaded dendritic cells, especially those dendritic cells which are obtainable by the method (1);

(4) a vaccine comprising dendritic cells as defined in (3); and (5) a method for finding advantageous conditions for the freezing of DCs, comprising the steps of:
  a) providing immature DCs;
  b) performing different cultures with the immature DCs in the presence of different maturing stimulants;
  c) then culturing the DCs in medium with or without cytokines, culturing without cytokines being preferred;
  d) determining the fraction of living cells after at least 1 day of culture in said medium with or without cytokines; and
  e) establishing that maturing stimulant which gave the highest survival rate.

In methods (1) and (2) of the invention, immature DCs are first cultured, a suitable maturing cocktail with one or more maturing stimulants being added to the culture medium. Suitable maturing stimulants include IL-1, such as IL-1β etc., IL-6, TNF-α, prostaglandins, such as $PGE_2$ etc., IFN-α, lipopolysaccharides and other bacterial cell products, such as MPL (monophosphoryllipid A), lipoteichoic acid etc., phosphorylcholine, calcium ionophores, phorbol esters, such as PMA, heat-shock proteins, nucleotides, such as ATP etc., lipopeptides, artificial ligands for Toll-like receptors, double-stranded RNA, such as poly-I:C etc., immunostimulant DNA sequences, CD40 ligand etc. According to the invention, it is particularly preferred for said culture medium or maturing cocktail to contain IL-1β, IL-6, $PGE_2$ and TNFα, or for said maturing cocktail to be monocyte-conditioned medium (MCM) or MCM supplemented with $PGE_2$. In a preferred embodiment of methods (1) and (2), the DCs can be loaded with antigen during or after the culturing step.

After maturing and optionally loading with antigen, the DCs are frozen in freezing medium which does not contain any heterologous serum, such as FCS. "Heterologous serum" within the meaning of this application is a serum which is not derived from the human species. However, according to the invention, it is possible to use both autologous serum or plasma (which is derived from the same human as the DCs) and allogeneic serum or plasma (which is derived from a different human than for the DCs).

Immature DCs within the meaning of this application are CD83 (and/or p55/fascin and/or DC-LAMP) negative (or only weakly positive and/or to a low percentage) leukocytes which express only low amounts, as compared to mature DCs, of class-I and Class-II MHC as well as adhesion or costimulatory molecules (e.g., in particular, CVD86, CD80, CD40), which will differentiate into mature DCs upon a suitable maturing stimulant.

Mature DCs within the meaning of this application are leukocytes which have developed from immature DCs under the action of a maturing stimulant, exhibit an enhanced expression of CD83 (and/or p55/fascin and/or DC-LAMP) and of class-II and class-I MHC molecules and adhesion or costimulatory molecules, especially of CD86, CD80, CD40. Further, the mature DCs exhibit a clearly increased T-cell stimulatory capacity as compared to immature DCs (e.g., in contrast to immature DCs, they exhibit a clear stimulatory activity in allogenic MLR even at a DC:T ratio of about ≤1:100); in addition, one characteristic of the mature DCs within the meaning of this application is the fact that these DCs are stable, i.e., will keep their properties of a mature phenotype and a strong T-cell stimulatory capacity even if cultured in the absence of cytokines for 1-2 days or longer. In contrast, DCs which have not yet fully matured are not stable and will differentiate into immature DCs or, e.g., into adherent macrophages.

The immature DCs can be provided from various known sources. The precursor cells of the immature DCs are usually non-proliferating CD14-positive mononuclear cells (PBMCs; monocytes) or proliferating CD34-positive cells. For example, PBMCs can be isolated from leucapheresis products. The PBMCs can be differentiated into immature DCs as described (Thurner et al. (1999) *J. Exp. Med.* 190, 1669). Thus, the PBMCs are cultured in the presence of IL-4 (or IL-13; Romani et al. (1996) *J. Immunol. Methods* 196, 137-151) and GM-CSF ("granulocyte-macrophage colony stimulating factor"). From CD14-positive monocytes, immature DCs can also be prepared by culturing in the presence of GM-CSF and IFNα (Santini et al. (2000) *J. Exp. Med.* 191, 1777-1788). From CD34-positive cells, immature DCs can be obtained by culturing in the presence of GM-CSF, SCF ("stem cell factor") and TNFα. The immature dendritic cells may also be obtained directly from fresh blood, such as described in Nestle et al. (1998) *Nat. Med.* 4, 328. Preformed CD11c+ and CD11c− DCs (O-Doherty et al. (1994) *Immunology* 82, 487-493) and M-DC8-DCs (Schakel et al. (1999) *Pathobiology* 67, 287-290) also exist in blood. These DCs may also be isolated from the blood and further used in the method according to the invention.

The preferred concentrations of the various maturing stimulants in the culture medium are within a range of from 0.1 ng/ml to 100 μg/ml, preferably from 1 ng/ml to 10 μg/ml. For the particularly preferred maturing cocktail of the present invention, the concentration of the maturing stimulants is from 0.1 to 100 ng/ml of IL-1β, from 0.1 to 100 ng/ml of IL-6, from 0.1 to 10 μg/ml of $PGE_2$, and from 0.1 to 100 ng/ml of TNFα (most preferably, the concentration of these special maturing stimulants is approximately 10 ng/ml of IL-1β, 10 ng/ml of IL-6, 1 μg/ml of $PGE_2$, and 10 ng/ml of TNFα). The concentrations stated are the final concentrations of the substances in the cell culture medium in which the DCs are cultured. One possibility of maturing the DCs in the presence of the mentioned active substances is to culture the immature DCs in the presence of monocyte-conditioned medium (MCM). MCM contains IL-1β, IL-6, $PGE_2$ and TNFα. It can be obtained by culturing PBMCs in medium without cytokines, as described, for example, in Romani et al. (1996) *J. Immunol. Methods* 196, 137. When the DCs are matured by MCM, the culture medium contains from 1 to 100%, preferably from 5 to 25%, of MCM. In another embodiment of the invention, the maturing of the DCs is effected by the addition of MCM and a defined amount of $PGE_2$. Namely, it has been found that variations in the capability of MCM to mature DCs in the best possible way can be counterbalanced by the addition of $PGE_2$ (preferably in the concentrations as stated above). However, according to the invention, it is preferred to mature the DCs by the addition of defined optimum amounts of the active substances IL-1β, IL-6, $PGE_2$ and TNFα. This means that the maturing composition is prepared from purified formulations of the individual active substances. Better results are achieved thereby as compared with the maturing with MCM or MCM+$PGE_2$. IL-1β, IL-6, $PGE_2$ and TNFα are available is GMP ("good manufacturing practice") grade. Usually, the maturing is effected by cultivation in the presence of the substances mentioned for at least one hour, preferably 2 hours and more preferably at least 6 hours. Particularly preferred according to the present invention are maturing times of from 6 to 96 hours, preferably from 18 to 36 hours (when leucapheresates are used as the starting material) or from 36 to 60 hours (when fresh blood or buffy coat is used as the starting material).

According to the invention, the DCs are loaded with at least one antigen or an antigen-antibody complex during and/or after the maturing step mentioned. According to the invention, the antigen loading can be effected during or after the freezing. If it is effected after freezing, the DCs are loaded with antigen only after thawing. However, preferred is loading with antigen prior to the freezing of the DCs. This has the advantage that the DCs are ready for use immediately after thawing.

Antigens within the meaning of this application are proteins, protein fragments, peptides and molecules derived therefrom (e.g., glycosylated compounds or compounds having other chemical modifications), but also the nucleic acid encoding them, viruses, whole prokaryotic or eukaryotic cells or fragments thereof, or apoptotic cells. "Loading with antigen" means a process which causes MHC molecules on the cell surface of the DCs to "present" peptides, i.e., the peptides form a complex with the MHC molecules. While a direct loading of the MHC molecules. is possible through specific peptides, proteins (or protein fragments) must first be processed, i.e., first taken up by the cell. After intracellular cleavage of the proteins and loading of MHCs with peptide, MHCII-peptide complexes are presented on the cell surface. Suitable antigens primarily include proteins or protein fragments. The proteins may be of native origin or have been prepared recombinantly. Due to the maturing and loading with protein antigen, MHCII-peptide complexes which comprise the peptide fragments of the antigen added form on the cell surface. The concentration of the protein antigen in the culture medium is usually from 0.1 to 100 µg/ml, preferably from 1 to 50 µg/ml, most preferred from 1 to 10 µg/ml.

If a protein (i.e., a polypeptide having more than 50 amino acid residues) is employed as the antigen, the loading should preferably be effected during the maturing of the DCs. This causes a particularly effective presentation of the antigen fragments by MHCII molecules. The protein (fragment) need not be present during the whole maturing period, but at least for part of the maturing period, both the maturing composition and the protein (fragment) should be simultaneously present. Examples of protein antigens include KLH (keyhole limpet hemocyanin) as a widely used positive control antigen. MAGE-3 protein as an example of a tumor antigen, and hepatitis B surface antigen (HBsAg) or HIV-1 gp-160 protein as examples of a protein appropriate for the treatment of viral diseases.

When the loading is performed with "short polypeptides" or protein fragments (e.g., short polypeptides with up to 50 amino acid residues which exactly fit into the MHC molecules on the DC surface), loading after maturing, namely prior to freezing or after rethawing, is also possible in addition to the above mentioned loading during maturing. In such a loading after maturing, the short polypeptides are added to washed DCs.

Another possibility of loading with antigen is the addition of apoptotic or lysed cells to the culture medium. The added cells can then be phagocytosed by the DCs. This method has the advantage that, in addition to MHC class II molecules, class I molecules can also be effectively loaded. For example, it has been shown that presentation also occurs on MHC class I molecules even when proteins (especially of particulate nature) are added. For example, instead of culturing the DCs in the presence of Mage-3 tumor protein or peptide, cell fragments (of necrotic or apoptotic tumor cells) which contain Mage-3 can be added to the DCs.

DCs may also be loaded with antigen by fusing DCs, for example, with tumor cells. Such a fusion can be achieved with polyethylene glycol or electroporation.

In another embodiment of the invention, the DCs are loaded with antigen by being transfected or virally infected. Nucleic acids coding for antigens are thereby introduced into the DCs or induced to expression. For example, a DNA or RNA transfection or infection with adenoviruses can be performed in a suitable way. Loading of the MHC class I molecules is also possible thereby. For example, RNA prepared from tumor cells can also be transfected. For transfection, usual methods, such as electroporation, can be employed.

As set forth above, specific antigen peptide (i.e., "short polypeptides") can be added during the maturing period or after the maturing period for directly loading MHC molecules of class I or II. The peptide antigen may be added to the cells before the maturing composition is added, but preferably, it is added simultaneously or thereafter. The antigen loading is preferably performed for at least 10 minutes, more preferably for 1 to 24 hours, most preferably for 3 to 12 hours.

The peptides (i.e., "short polypeptides") usually have at least 8 amino acids. Preferably, such peptides have from 8 to 12 amino acids (MHCI) or from 8 to 25 amino acids (MHCII). The concentration of the peptide in the culture medium for loading is usually from 0.01 to 1000 µM, preferably from 0.1 to 100 µM, most preferably from 1 to 20 µM.

All peptides which can be presented by MHC molecules can be considered as peptides to be employed. Preferred are peptides which are derived from proteins derived from pathogens. These may also be peptides which exhibit variations of the naturally occurring amino acid sequence. Such variations are usually one or two amino acid substitutions. Examples of peptide antigens are the influenza matrix peptide (IMP) having the amino acid sequence GILGFVFTL (SEQ ID NO: 1) or the Melan-A-analogue peptide having the sequence ELAGIGILTV (SEQ ID NO: 2). Examples of other possible peptides are represented in FIG. 26.

In addition to "peptide/protein pulsing", "peptide/protein transloading" may also be performed to load DCs with antigen.

As stated above, the DCs may also be loaded with antigen-antibody complexes. Suitable antigens for this purpose include all the antigens mentioned above. "Antigen-antibody complexes" according to the present invention are complexes of such antigens with suitable antibodies, e.g., antigen-IgG or antigen-IgE complexes. The loading of DCs with such antigens is described in Reynault, A. et al., J. Exp. Med. 189(2): 371-80 (1999), which is included herein by reference.

After the maturing and optionally antigen loading of the DCs, the mature DCs can be frozen in freezing medium. In addition to the serum component, the freezing medium may additionally contain one or more cryoprotectants (e.g., from 0.1 to 35% (v/v), preferably from 5 to 25% (v/v)). Suitable cryoprotectants preferably include the following compounds: DMSO, glycerol, polyvinylpyrrolidone, polyethylene glycol, albumin, choline chloride, amino acids, methanol, acetamide, glycerol monoacetate, inorganic salts etc. The preferred cryoprotectant is DMSO, which is preferably contained in the freezing medium in a concentration of from 5 to 25% (v/v), more preferably from 10 to 20% (v/v), most preferably about 10% DMSO. The freezing medium may contain a non-heterologous serum component, preferably in a concentration of from 2 to 90% (w/v), preferably from 5 to 80% (w/v), wherein human serum albumin, preferably in a concentration of from 10 to 30% (w/v), is particularly preferred. More preferably, however, the freezing medium contains autologous serum or plasma instead of human serum albumin. It may also contain human allogenic serum or pool serum. Also, the freezing medium may contain as an additive one or more polyol compounds derived from carbohydrates, especially those selected from glucose, dextrane, sucrose, ethylene glycol, erythritol, D-ribitol, D-mannitol, D-sorbitol, inositol, D-lactose etc., preferably in a concentration of from 2 to 30%, more preferably from 5 to 10%, most preferably about 5% (w/v). The most preferred freezing medium is pure autologous serum with about 10% DMSO and about 5% glucose. Usually, the cells are centrifuged off prior to freezing to be concentrated and taken up in freezing medium.

The preferred concentration of cells in the freezing medium is from 1 to $100 \times 10^6$ cells/ml, the most preferred concentration being from about $5 \times 10^6$ cells/ml to $20 \times 10^6$ cells/ml.

It has also been found that the survival rate of DCs is increased by contacting the DCs with an anti-apoptotic molecule prior to freezing or after thawing. Therefore, in a preferred embodiment of the method according to the invention, The DCs are contacted prior to freezing or after thawing with a molecule capable of inhibiting apoptosis. Preferred anti-apoptotic molecules include CD40 ligand (CD40L) (Morris et al. (1999) J. Biol. Chem. 274: 418), TRANCE (Wong et al.

(1997) *J. Exp. Med.* 186: 2075) or RANKL (Anderson et al. (1997) *Nature* 390: 175). Preferably, at least one of the molecules is added to the culture medium prior to freezing or after thawing of the DCs for at least 10 min, preferably at least 1 hour, more preferably at least 4 hours. Preferred concentrations in the culture medium are 1 ng/ml to 5 µg/ml (RANKL/TRANCE) and 1 ng/ml to 1 µg/ml (CD40L). Particularly preferred concentrations are from 0.5 to 1 µg/ml (RANKL/TRANCE) and from 0.1 to 0.5 µg/ml (CD40L).

In a preferred embodiment of the method, the DCs are further cultured in the presence of immunosuppressive interleukin-10 (IL-10) or other immune/maturing modulators, such as vitamin D3 and its derivatives, fumaric acid and derivatives thereof, such as esters etc., mycophenolate mofetil etc. Cells thus treated are not employed for the stimulation of the immune system, but rather a tolerance against particular antigens is to be induced. The concentration of these modulators and of IL-10 in the medium is from 1 to 1000 ng/ml, preferably from 10 to 100 ng/ml.

According to embodiment (4), the present invention also relates to a vaccine obtainable by the method according to the invention. In addition to the mature antigen-loaded DCs, the vaccine according to the invention may further contain pharmaceutically acceptable adjuvants. After the thawing of the vaccine according to the invention, various substances may be added which are pharmaceutically acceptable and advantageous for administration.

According to embodiment (3), the invention also relates to frozen mature antigen-loaded dendritic cells. These cells according to the invention may be part of a pharmaceutical composition which contains usual additives suitable for the administration to humans, in addition to the cells.

The present invention for the first time provides a vaccine which contains mature antigen-loaded DCs and can be frozen. An essential advantage of the invention is that the survival rate of the DCs after thawing is very high. After the thawing of the frozen DCs, more than 75%, preferably more than 85%, of surviving DCs are usually obtained, based on the number of frozen DCs. Such high survival rates of thawed DCs have not been achieved previously without the addition of FCS. However, this is an important precondition for achieving an effective immunostimulation. A substantial advantage of the freezing of mature antigen-loaded DCs is that multiple aliquots of a vaccine can be prepared and frozen. Thus, the vaccine is immediately available when needed and can be applied without lengthy culturing steps within a very short time. By loading the mature DCs with the antigen only after the freezing and rethawing, it is possible to load the DCs variably depending on the respective circumstances. For example, when an overstimulation or allergy against one of the peptides employed for vaccination is developing, this peptide can be omitted in the loading.

Surprisingly, it has been found that, for finding suitable methods for the freezing of DCs, it is not sufficient to vary the immediate freezing parameters, such as freezing medium and cooling rate, and to determine the survival rate immediately after thawing. This immediate survival rate not necessarily corresponds to the survival of freshly prepared DCs during several days of culture in the absence of cytokines.

Rather, the maturing process or the maturing stimulant employed prior to freezing also play an important role to the survival of the cells. Thus, the invention is also based on the recognition that the maturing stimulant according to the invention not only leads to a full DC maturation, but also yields DCs which can survive better than DCs which have been matured by other stimulants. To date, the maturing stimulant was not considered at all in view of the freezing.

It has also been found that an excellent method for optimizing the process for the freezing of DCs is to mature DCs by means of different maturing stimulants and then to test the survival after culture in complete medium without any addition of cytokine as a read-out. The maturing stimulant which induces the most viable DCs is used for the preparation of DCs which are then frozen.

Therefore, another aspect of the invention is a method for finding advantageous conditions for the freezing of DCs wherein immature DCs are provided and cultured in the presence of various maturing stimulants, the cells are subsequently cultured in medium with or without cytokines, preferably without cytokines, the fraction of surviving cells is determined after at least one day of culture in a medium with or without cytokines, and finally that maturing stimulant which gave the highest survival rate of DCs is determined. This maturing stimulant is then used for the preparation of DCs which are frozen. Preferably, the number of living cells is determined only after at least 2 days of culture in a medium without cytokines, most preferably after at least 3 days.

BRIEF DESCRIPTION OF THE DRAWINGS

FIG. 18A shows the result of the determination of the total number of DCs after loading with apoptotic tumor cells and subsequent cryoconservation.

FIG. 28 shows MHC class I and II restricted melanoma and influenza viral peptides which can be employed in the method of the present invention. Abbreviations: AS=amino acids, NT=nucleotides, NP=nucleoprotein, ana*=analogue peptide

Figure 1:
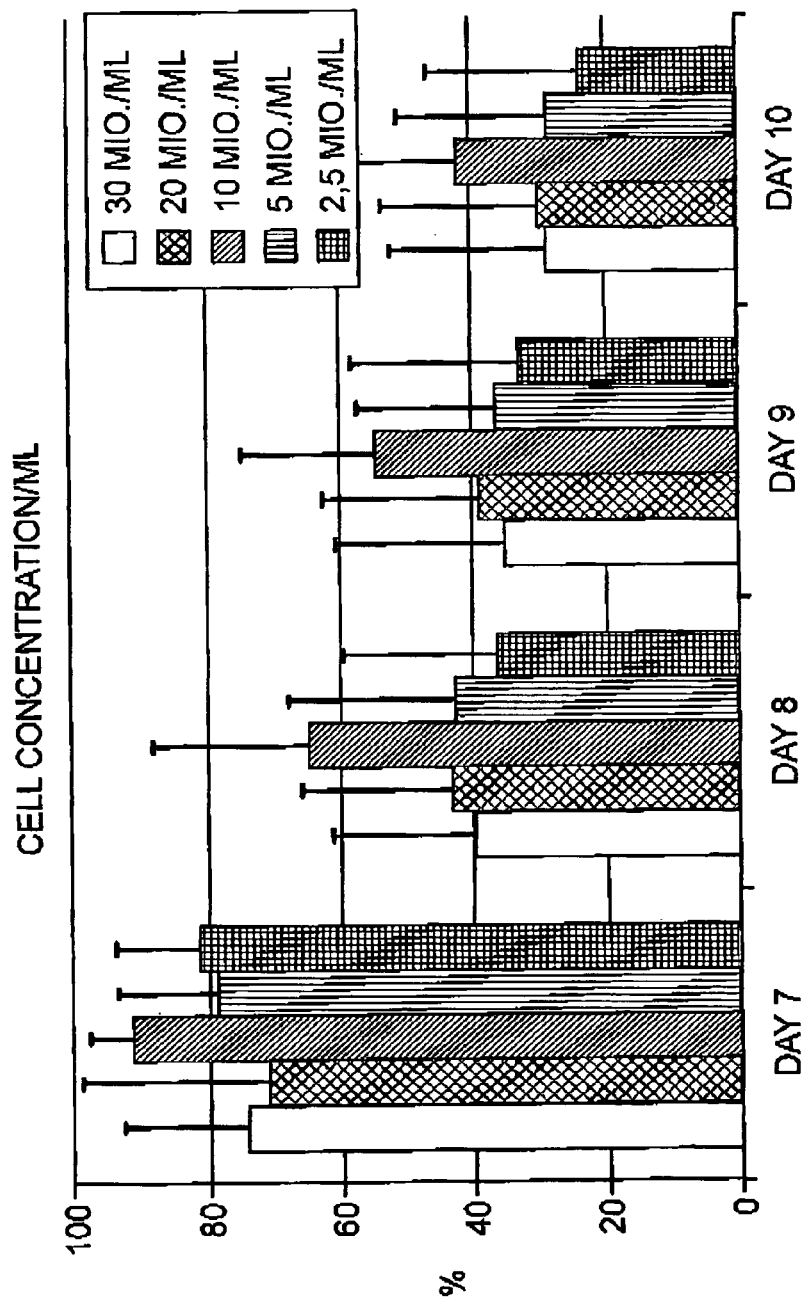
FIG. 1 shows the influence of the cell concentration in the freezing vessels on the yield of DCs after thawing. Mature DCs were prepared from leucapheresis products from healthy adults, wherein adherent monocytes were first converted into immature DCs by six days of culture in GM-CSF+IL-4, followed by maturing for one day by a four-component cocktail consisting of TNFα+IL-1β+IL-6+PGE$_2$ (see Example 1). Mature (day 7) DCs were frozen at a freezing rate of −1° C./min in pure autologous serum+10% DMSO+5% glucose at different cell densities (number of DCs/ml). After the thawing of the mature DCs, the yields of living DCs (stated as the percent fraction of the number of frozen DCs) were determined immediately (=d7) and after several days of culture (after 1 day=d8, after 2 days=d9, etc.). The latter determination was performed in complete medium, but without the addition of GM-CSF or IL-4, since this hard "wash-out test" is an established method for determining whether DCs have actually been fully matured and are stable. Freezing at 10×10$^6$ mature DCs/ml yielded the best results (p<0.05 on day 7, p<0.01 on all other days; n=3).

[a] Most frequent DR4 subtype, approximately 80%
[b] Most frequent DR4 subtype, approximately 80%
[c] To date, 30 different HLA DR13 alleles have been described. Restriction for DRB1*1301 and DRB1*1302, which together make up 80% of the DR13 alleles, was shown. It is possible that other DR13 alleles also present the peptide.
[d] The epitope is presented less effectively by this second HLA DP4 allele as compared to the allele DPB1*0401.

DETAILED DESCRIPTION OF THE INVENTION

The following Examples are intended to further illustrate the invention, but without any limitation thereto.

Example 1

The survival rates of freshly prepared immature DCs and of DCs matured by different maturing stimulants were determined.

The following different maturing stimulants were tested:

Monocyte-conditioned medium, prepared and used as described (Thurner et al. (1999) *J. Immunol. Methods* 223, 1);
  10 ng/ml TNFα;
  10 ng/ml TNFα+1 µg/ml PGE$_2$;
  10 ng/ml TNFα+10 ng/ml IL-1β+100 U/ml IL-6+1 µg/ml PGE$_2$ ("maturing cocktail");
  up to 1.0 µg/ml of LPS of *Salmonella abortus* equi;
  double-stranded RNA (poly-I:C, 20 µg/ml);
  from 50 to 1000 ng/ml CD40L.

Preparation of monocyte-derived DCs from PBMCs: As a complete medium, RPMI 1640 with 20 µg/ml gentamicin, 2 mM glutamine and 1% heat-inactivated (56° C., 30 min) autologous human plasma was used. Leucapheresis products were prepared as monocyte separation products from healthy cytapheresis donors as described (Thurner et al. (1999) *J. Immunol. Methods* 223, 1). Peripheral blood mononuclear cells (PBMCs) were then isolated by centrifugation in lymphoprep, and DCs were prepared from plastic-adherent fractions of the PBMCs as described (Thurner et al. (1999) *J. Immunol. Methods* 223, 1). For this purpose, immature DCs were obtained by a culture in complete medium with recombinant human GM-CSF (800 U/ml) and IL-4 (500 U/ml). On day 6, the different maturing stimulants mentioned above were added to the DCs, and on day 7, the mature DCs were harvested and further cultured for another two days in the absence of cytokines. The survival rates after two days of culture in percent of the sown DCs were:

38.25% for immature DCs; 76.2% for (IL-1β+IL-6+PGE$_2$+TNFα)-matured DCs;
13.5% for TNFα-matured DCs;
37.0% for (TNFα+PGE$_2$)-matured DCs;
31.8% for (poly-I:C)-matured DCs; and
49.6% for CD40L-matured DCs (at 500 ng/ml).

The differences were statistically significant.

Example 2

Mature (day 7) DCs were frozen as follows: DCs were resuspended in cryovessels at different concentrations (5, 20, 40, 60 and 100×10$^6$ per ml) either in pure autologous serum or in 20% human serum albumin (HSA; consisting of 1000 ml of electrolyte solution supplemented with 200 g of human plasma proteins with at least 95% of albumin; DRK Blutspendedienst Baden-Wurttemberg, Baden-Baden, Germany). The DC suspension formed was mixed 1:1 with the different freezing solutions described hereinafter and then immediately transferred into a 1.0 or 1.8 ml cryovessel. Immediately thereafter, the vessels were cooled down to −80° C. in a "Cryo Freezing Container" (Nalgene Cryo 1° C. Freezing Container, cooling rate −1° C./min) and finally transferred into the gas phase of liquid nitrogen, where they were kept for up to seven months.

a) Freezing Media

HSA+DMSO±glucose (consisting of 20% HSA solution (see above)+10, 15, and 25% (v/v) DMSO±glucose (Glukosteril 40%™, Fresenius, Germany, active ingredient: glucose monohydrate) at 2, 4, 6, 10, 20 or 30% (v/v));

serum+DMSO±glucose (pure autologous serum+20% (v/v) DMSO±glucose added at 2, 4, 6, 10, 20 or 30%);

Erythrocyte Freezing Solution™ (Erythrocyte Freezing Solution™ (Fresenius, Dreieich, Germany), consisting of 38% glycerol, 2.9% sorbitol and 0.63% sodium chloride in sterile water);

Cell Processing Solution™+DMSO (Fresenius, Dreieich, Germany, consisting of 6% hydroxyethylstarch in 0.9% sodium chloride, usually used for the sedimentation of erythrocytes)+10 or 15% (v/v) DMSO.

b) Thawing Conditions

For the thawing of frozen mature (day 7) DCs, the following four methods were examined:

1. DCs were thawed in a water bath at 56° C., then incubated without washing in 10 to 20 ml of ice-cold complete medium (supplemented with 800 U/ml of GM-CSF and 500 U/ml of IL-4) in Teflon dishes (Rotilabo boxes, Roth, Karlsruhe, Germany) at 37° C. and 5% CO$_2$ for two hours, then harvested and centrifuged for 10 minutes at 150×g and 22° C. Subsequently, the cells were counted and again sown on Teflon dishes in complete medium with GM-CSF and IL-4 (cell density 1×10$^6$ per ml) and cultured over night. On the next day, the cells were harvested for further use.

2. Frozen mature (day 7) DCs were thawed as described under 1, and after a resting period of two hours at 37° C. and 5% CO$_2$ on Teflon dishes, the cells were harvested (centrifugation for 10 min at 150×g and 22° C.) for further use.

3. Frozen mature (day 7) DCs were thawed as described under 1, and after a resting period of two hours at 37° C. and 5% CO$_2$ on tissue culture dishes (Falcon Becton Dickinson Labware, New Jersey, USA), the cells were harvested (centrifugation for 10 min at 150×g and 22° C.) for further use.

4. Frozen mature (day 7) DCs were thawed in a water bath at 56° C., then added to 10 ml of ice-cold "Hank's Balanced Salt Solution" (Bio Whitaker) and immediately centrifuged for 12 min at 133×g and 4° C. Subsequently, the cells were harvested for further use.

c) Establishing of DC Survival Rate

The survival rate of frozen and rethawed DCs was examined by culturing in complete medium without the addition of GM-CSF and IL-4 over at least 4 days (="wash-out test") and compared with the survival rate of DCs which had been freshly prepared from non-frozen or frozen aliquots of PBMCs as described (Thurner et al. (1999) *J. Immunol. Methods* 223, 1). The respective amounts of living DCs were determined by a cell counter (Cassy Cell Counter and Analyser System, Model TT, Schrfe System, Reutlingen, Germany; this system uses "pulse area analysis" and allows the determination of cell counts, cell size and volume as well as whether living cells are present) and as a control also through standard trypan blue staining.

First, the influence of the DC concentration was examined, wherein freezing at $10 \times 10^6$ mature DCs/ml yielded the best results. The result is shown in FIG. 1.

Further, the influence of the DMSO concentration (5 to 12.5% v/v final concentration) was examined. A change of the DMSO concentration had no significant effect on the survival rate of thawed DCs.

Figure 2:
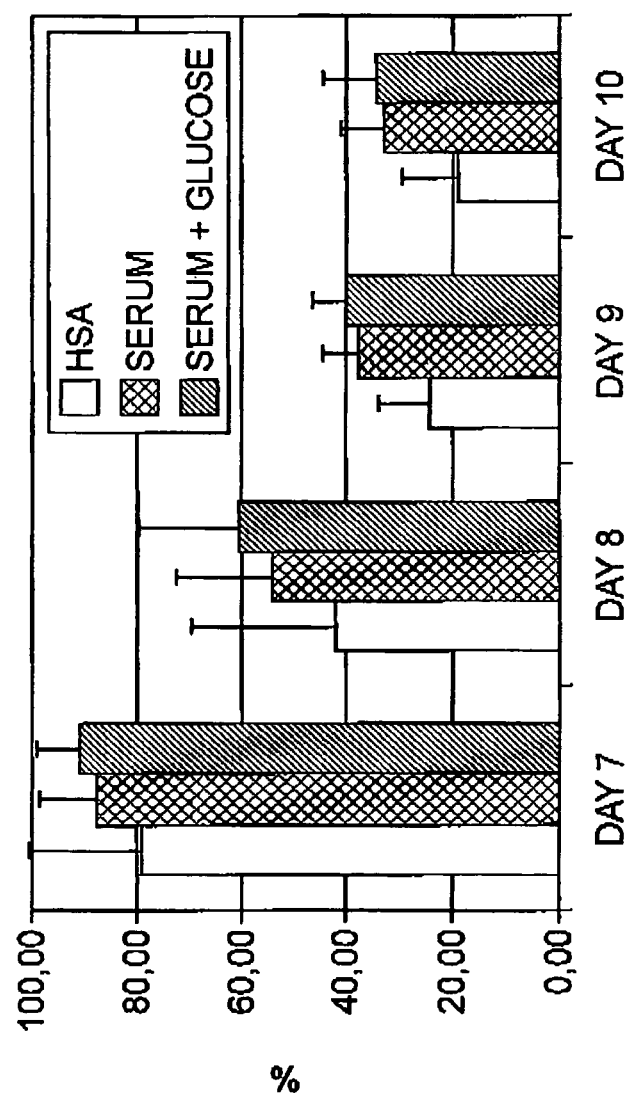
FIG. 2 shows the influence of various freezing media on the DC yield after rethawing. DCs were prepared as described in the legend of FIG. 1, and aliquots were frozen at a concentration of 10×10$^6$ DCs/ml in HSA+10% DMSO, in autologous serum+10% DMSO, and in autologous serum+10% DMSO+5% glucose (final concentrations). The DC yields after freezing and rethawing were determined as described for FIG. 1. Freezing in autologous serum+10% DMSO+5% glucose yielded the best results (p<0.05 on day 8; n=4).

Further, it was examined whether HSA or pure autologous serum yielded better survival rates, and whether an addition of glucose (final concentrations v/v of 1, 2, 3, 5, and 15%) improves the survival rate. The result is shown in FIG. 2. The survival rate of DCs after several days was reproducibly increased if HSA was replaced by autologous serum. An addition of glucose in a final concentration of 5% (v/v) further improved the results.

Various commercially available freezing media, such as Erythrocyte Freezing Solution™ or Cell Processing Solution (Fresenius) were also examined. However, these yielded worse results as compared with the freezing media already tested.

Also, the various thawing conditions mentioned under b) were examined for minimizing the stress to which the cells are subjected after thawing. None of the four methods tested showed a clear superiority over the others.

Mature (day 7) DCs were prepared as described in Example 1 and frozen under the following conditions:

Cooling rate 1° C. per min in pure autologous serum+10% DMSO+5% glucose at a cell density of $10 \times 10^6$/ml. After at least three hours of storage in the gas phase of liquid nitrogen, the cells were thawed. After thawing, the percentage of living DCs was directly determined (=D7). Aliquots of the DCs were sown, and the survival rates were determined after up to 4 days in culture in medium without cytokines ("wash-out test") as described in Example 1c) (n=20). The result is shown in the following Table.

Yield of Frozen/Thawed DCs after Thawing (Day 7) and in "Washout Tests" (Days 8 to 11).

| Days | Yield in % | 95% confidence interval |
| --- | --- | --- |
| 7 | 93.3 | 100.0-85.8 |
| 8 | 74.1 | 81.7-66.6 |
| 9 | 63.3 | 70.8-55.7 |
| 10 | 55.8 | 63.4-48.2 |
| 11 | 47.1 | 57.9-36.2 |

Example 3

Figure 3:
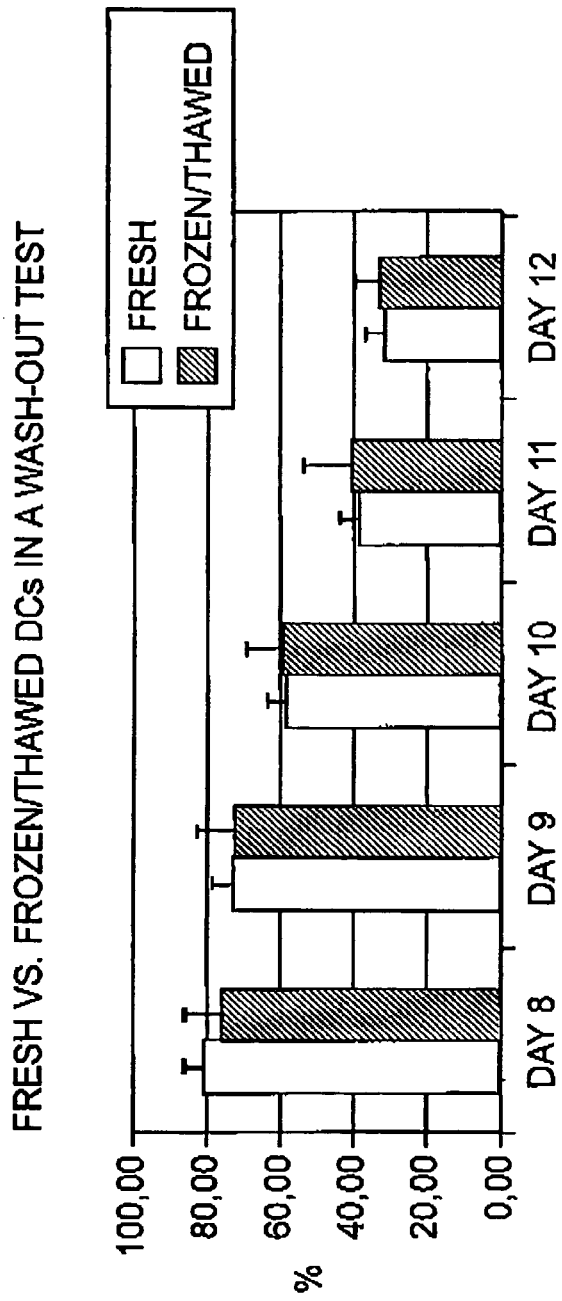
FIG. 3 shows the survival rate of fresh DCs in comparison with that of frozen and rethawed DCs in "wash-out tests". Mature d7 DCs were prepared as described for FIG. 1, and then freshly prepared as well as frozen (−1° C./min in pure autologous serum+10% DMSO+5% glucose at a cell density of 10×10$^6$ DCs/ml) and rethawed after more than 3 hours of storage in the gas phase of liquid nitrogen) DCs were cultured for several days in medium without cytokines ("wash-out test") as described in FIG. 1. The yields of living DCs are stated as percent fractions of the total number of DCs sown into the wells on day 7. There was no statistically significant difference between freshly prepared and frozen/thawed DCs (n=4).

Optimally matured and frozen DCs are equivalent to freshly prepared DCs with respect to survival rate and T-cell stimulatory activity.

a) First, it was examined whether the survival rate of frozen and rethawed DCs is comparable with the survival rate of freshly prepared DCs from the same donor. Thus, the "washout test" was used as described in Example 2c). The result is shown in FIG. 3. It was found that there is no difference between thawed DCs and freshly prepared DCs from the same donor.

Figure 4B:
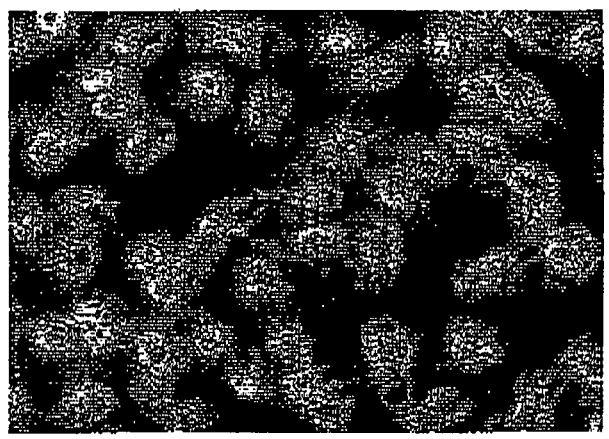
FIG. 4 shows that the freezing and rethawing does not change the characteristic morphology of mature DCs. Mature d7 DCs prepared as described for FIG. 1 were either immediately further cultured for another 2 days or were further cultured after freezing, at least 3 hours of storage in the gas phase of liquid nitrogen and rethawing. Even after 48 hours of further culture in the absence of cytokines ("wash-out test"), the non-frozen (left) and frozen/rethawed (right) DCs remained stable non-adherent cells.
Figure 4A:
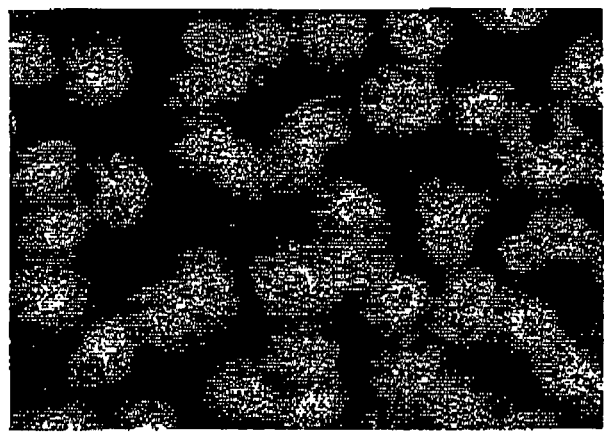
Figure 5:
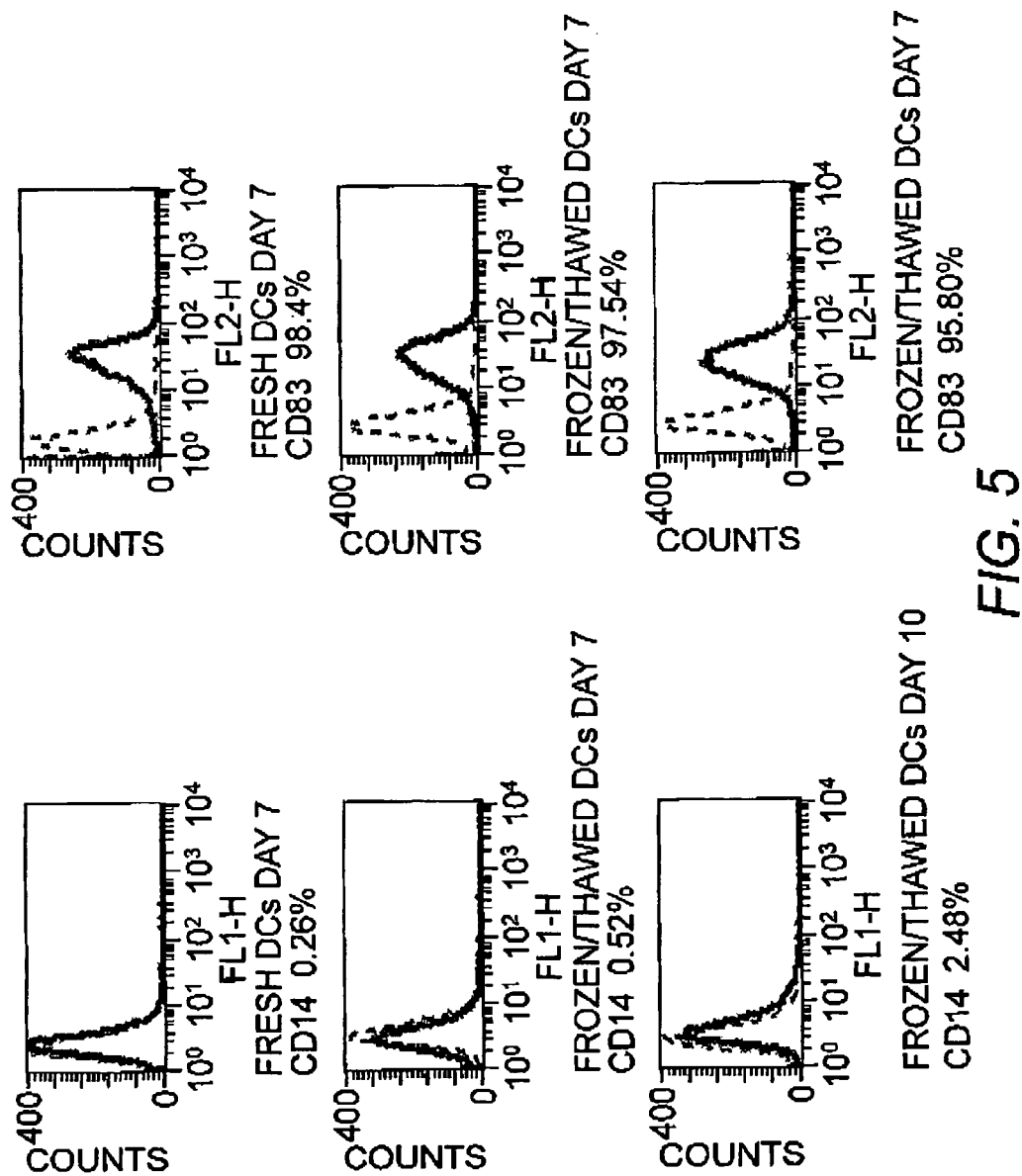
FIG. 5 shows that the freezing and rethawing does not change the characteristic phenotype of mature DCs. Mature d7 DCs freshly prepared as described for FIG. 1 were phenotyped by a FACS analysis (fresh DC, day 7). Aliquots were frozen, stored for at least 3 hours in the gas phase of liquid nitrogen, rethawed, and subsequently their phenotype was determined immediately (DCs frozen/rethawed d7) or after another 3 days in culture ((DCs frozen/rethawed d10) in the absence of cytokines ("wash-out test"). Frozen/rethawed mature d7 DC maintained the characteristic phenotype of mature DCs (CD14−, CD83 homogeneously ++) even after the removal of cytokines and further culture for 3 days.

Also, the morphology and the phenotype of thawed DCs were compared with those of freshly prepared DCs. The morphology of the cells was examined with an inverted-phase microscope (Leika DM IRB, Leika Mikroskopie and Systeme GmbH, Wetzlar, Germany) and recorded by photography. The phenotype of the cell populations was examined by a series of monoclonal antibodies and examined on a FACScan device (Becton Dickinson, New Jersey, USA) as described (Thurner et al. (1999) *J. Immunol. Methods* 223, 1). Dead cells were sorted out due to their light-scattering properties. The result is shown in FIGS. 4 and 5. Frozen and rethawed DCs keep their characteristic morphological properties and their phenotype over several days.

b) Then, it was examined whether rethawed DCs also maintain their functional properties.

Figure 6:
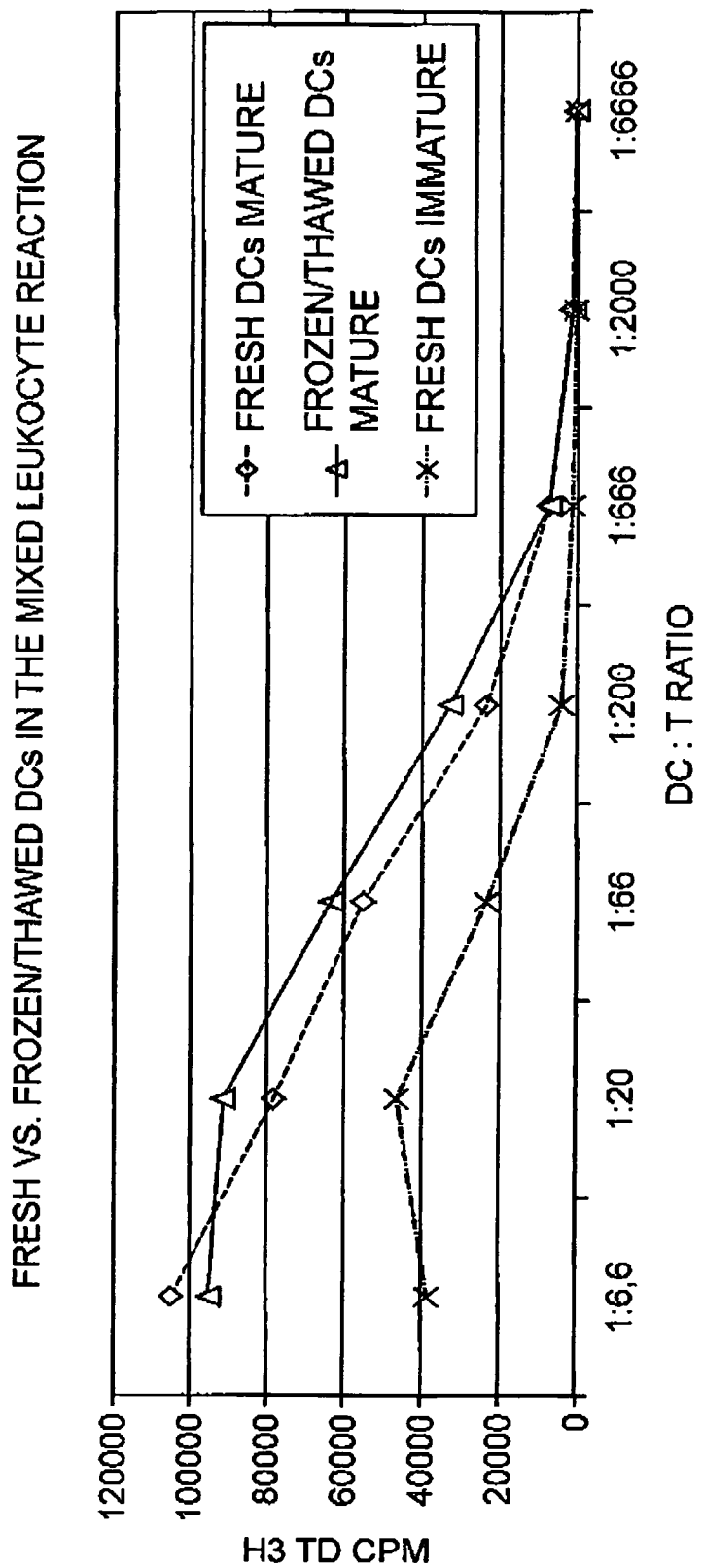
FIG. 6 shows that the freezing and rethawing does not change the stimulatory capacity of mature DCs in the primary allogenic MLR ("mixed leucocyte reaction"). Mature d7 DCs were prepared as described for FIG. 1, and the allostimulatory potency of freshly prepared non-frozen DCs was compared with that of an aliquot of these DCs which had been frozen and rethawed (after 3 hours of storage in liquid nitrogen).

1. Thus, it was examined whether rethawed DCs can induce primary allogenic MLRs as effectively as freshly prepared, non-frozen mature DCs. This test was performed as described (Thurner et al. (1999) *J. Immunol. Methods* 223, 1). DCs were added in graded doses to $2 \times 10^5$ allogenic T cells per well in flat-bottomed 96-well plates and co-cultured for 4 to 5 days in RPMI 1640 (supplemented with gentamicin, glutamine and 5% allogenic heat-inactivated human serum (pool serum)), and the proliferation was determined by the addition of $^3$H-thymidine (4 µCi final concentration/ml) for the last 12 to 16 hours of the co-incubation. The result is shown in FIG. 6. Frozen and rethawed DCs induce primary allogenic MLRs as effectively as freshly prepared mature DCs.

2. It was also examined how effectively frozen and rethawed DCs can induce cytotoxic T lymphocytes (CTLs). For this purpose, the induction of IMP (influenza matrix peptide) specific CTLs by IMP-pulsed mature DCs was measured. This approach is specific for mature DCs when performed in the absence of T cell assistance and exogenic IL-2. The induction of CD8+ T cells specific for influenza matrix A2.1 peptide (IMP) or Melan-A A2.1 peptide was effected by the stimulation of purified CD8+ T cells (isolated from PBMCs by magnetic cell sorting/MACS with CD8 microbeads according to the supplier's specifications, Miltenyi Biotec, Bergisch Gladbach, Germany), or in other experiments of non-adherent PBMC fractions with DCs (prepared from autologous PBMCs from HLA-A2.1+donors) which were either unpulsed or pulsed with HLA-A2.1 restricted IMP (GILGFVFTL [SEQ ID NO: 1], 10 µM for 1 hour at 37° C. at $1 \times 10^6$ DCs/ml of complete medium) or Melan-A-analogue peptide (ELAGIGILTV [SEQ ID NO: 2], 10 µM) at a DC/T ratio of 1:10 or 1:30 for 7 days without the addition of cytokines. CTLs were quantified by a standard lysis assay (Bhardwaj et al. (1994) *J. Clin. Invest.* 94, 797) or by tetramer staining at 37° C. (Whelan et al. (1999) *J. Immunol.* 163, 4342). The target cells for the standard 4-hour $^{51}$Cr-release assay, which was performed at different effector/target cell ratios, were IMP-pulsed (10 µg/ml for 1 hour at 37° C.) T2A1 cells, unpulsed T2A1 cells and K562 target cells (all .sup.51Cr-labeled). All experiments were performed with an 80 fold excess of K562 cells in order to block the natural killer cell activity. The specific lysis in % was calculated by the formula (specific release–spontaneous release)/(maximum release–spontaneous release)×100. Soluble IMP and Melan A/HLA A2.1 tetramers were prepared, and the formation of T cells was analyzed by flow cytometry at 37° C. as described (Whelan et al., 1999). 1 µl of tetramer (0.5 to 1 mg/ml) was added to $2 \times 10^6$ cells in about 60 µl (volume remaining in the vessel after centrifugation and pouring of the supernatant) of medium consisting of RPMI 1640 supplemented with gentamicin, glutamine and 5% allogenic heat-inactivated human serum (pool serum) for 15 min at 37° C. Subsequently, the cells were cooled down without washing and incubated on ice for 15 min with a triply stained monoclonal antibody against human CD8 (Caltag Laboratories, Burlingame, Calif.). After three washing steps, the cells were analyzed on a FACScan device (Becton Dickinson).

Figure 7:
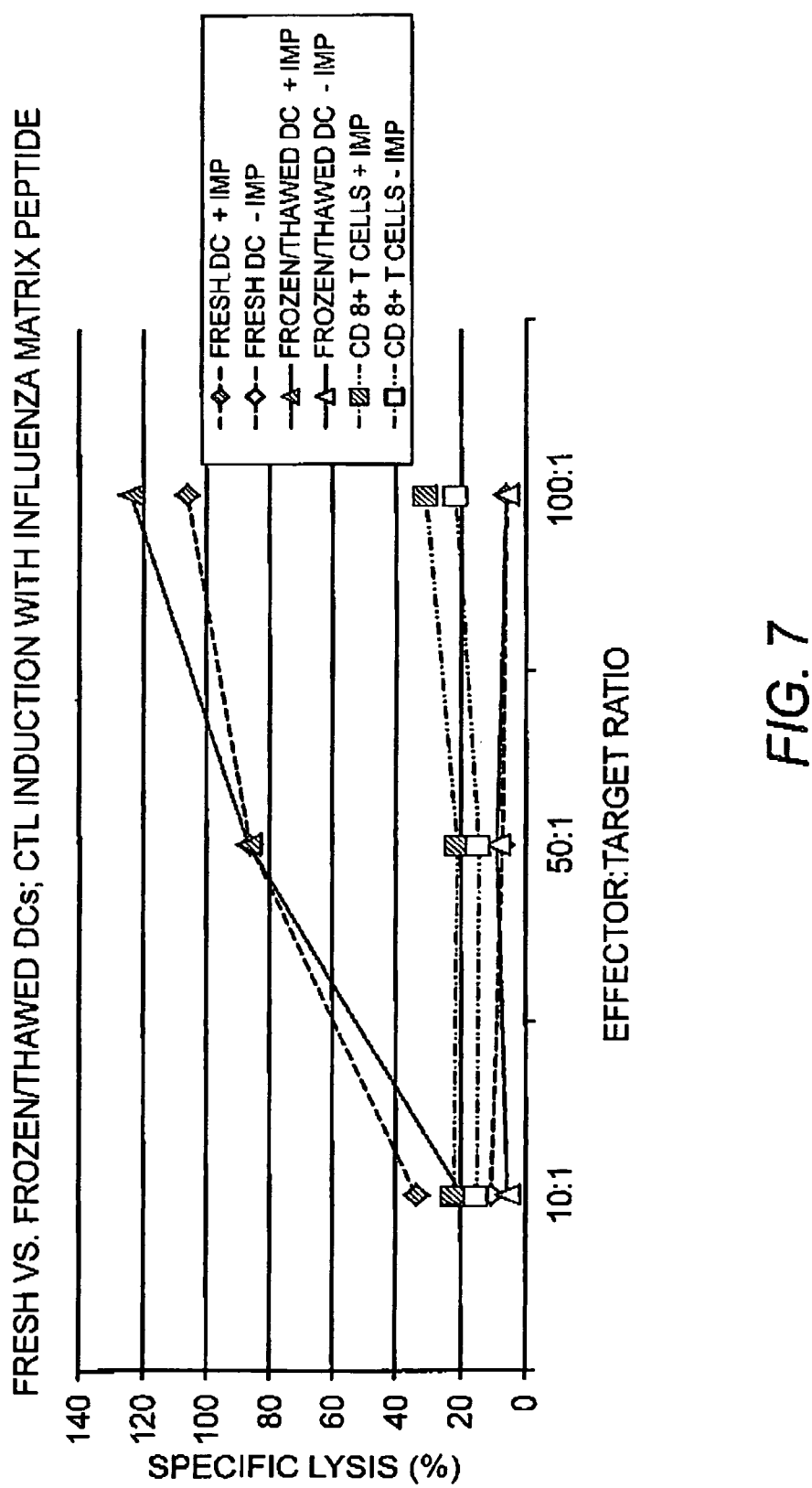
FIG. 7 shows that the freezing and rethawing does not change the ability of mature DCs to induce a strong IMP-specific CTL response. Freshly prepared or frozen/rethawed HLA-A2.1+ mature d7 DCs were loaded with influenza matrix peptide (=IMP) GILGFVFTL (SEQ ID NO: 1) or left untreated and cultured with autologous CD8+ T cells (T:DC ratio=10:1) without adding any cytokines. Additionally, purified CD8+ T cells were cultured without DCs±addition of IMP. After 7 days, the T cells were harvested and examined for their cytologic activity using a standard $^{51}$Cr release assay. T2 cells pulsed without or with 10 μg/ml of IMP served as the target cells.
Figure 8:
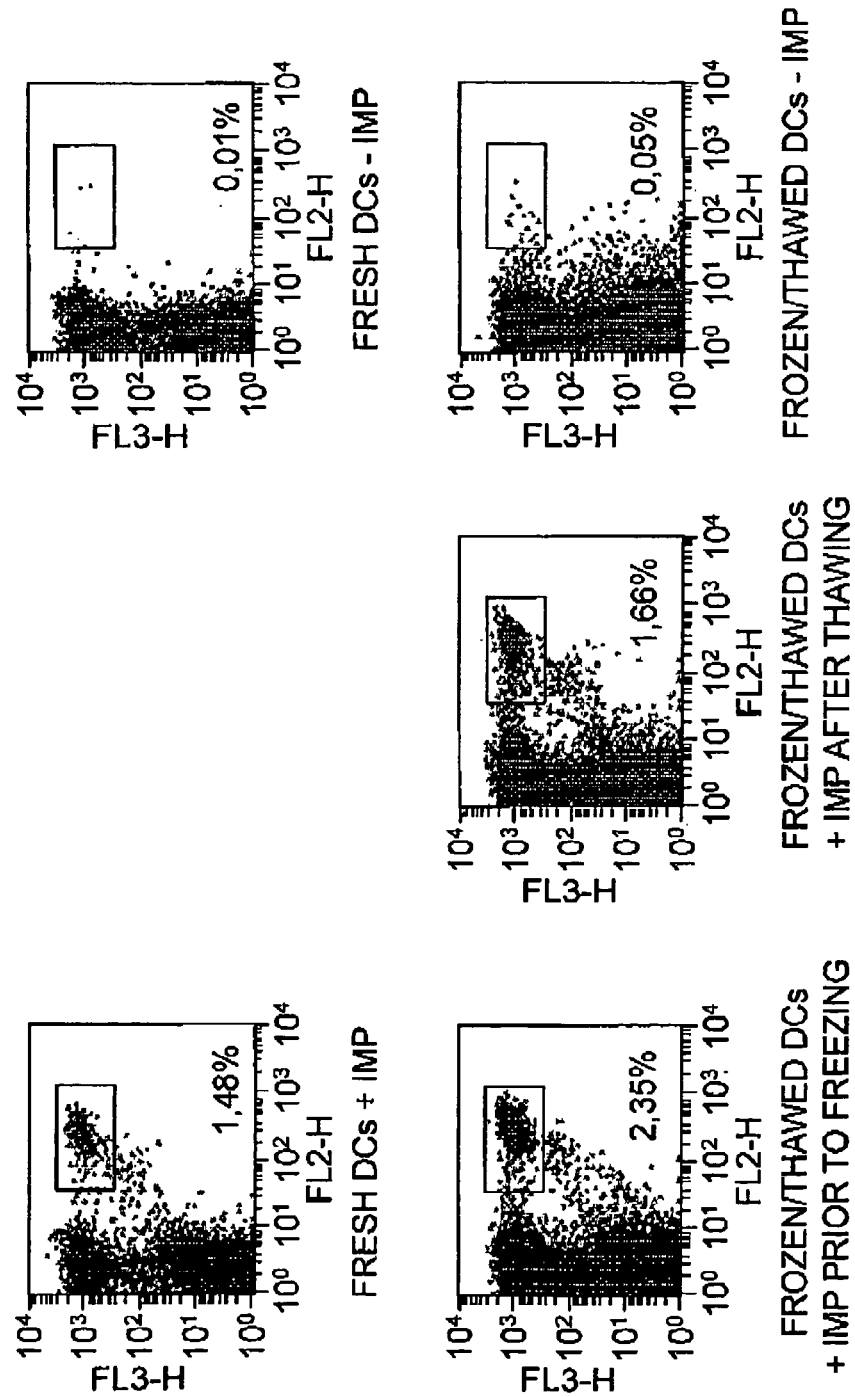
FIG. 8 shows that the freezing and rethawing does not change the ability of mature DCs to induce a strong IMP-specific CD8+ T cell response (HLA-A2.1/peptide tetramer analysis). Freshly prepared or frozen/rethawed HLA-A2.1+ mature d7 DCs were loaded with IMP (in the case of frozen/rethawed cells, prior to freezing or after thawing) or left untreated and co-cultured for 7 days with autologous non-adherent fractions of PBMCs (PBMC:DC ratio=30:1) without adding any cytokines, harvested and double-stained with HLA-A2.1/IMP tetramers (X axis) and anti-CD8 (Y axis). The expansion of IMP-peptide-specific CD8+ T cells (the percentage of tetramer-binding CD8+ T cells is stated in the Figure) is comparable for fresh and frozen DCs. Loading DCs prior to freezing or after thawing does not make a difference.

The result is shown in FIGS. 7 and 8.

The freezing and thawing of DCs does not change the capability of mature DCs of inducing a strong IMP-specific CLT response. Also, the freezing and thawing does not change the capability of mature DCs of inducing strong IMP-specific CD8+ T cell responses, as shown by the HLA-A2.1/peptide tetramer analysis.

These experiments show that, after the freezing and thawing, living DCs were obtained which are absolutely equivalent with freshly prepared DCs.

Example 4

To achieve an increased survival rate of the frozen and rethawed DCs, the following different anti-apoptotic stimulants were added to the DCs in different concentrations and at different times:

1. Recombinant murine or human trimeric TRANCE (Wong et al. (1997) *J. Exp. Med.* 186, 2075) at 100, 200, 500 ng/ml;
2. RANKL (Anderson et al. (1997) *Nature* 390, 175) at 10 ng/ml, 50 ng/ml, 100 ng/ml and 1 µg/ml;
3. Trimeric soluble CD40L (Morris et al. (1999)*J. Biol. Chem.* 274, 418) at 50, 100 and 500 ng/ml.

The DCs were subjected to the different anti-apoptotic stimulants at 37° C. over night for the last 12-16 h of culture prior to freezing, for 4 h prior to freezing (cell density $1 \times 10^6$ in complete medium with GM-CSF and IL-4), and also for 4 h after thawing (cell density $1 \times 10^6$ in complete medium with GM-CSF and IL-4).

Figure 9:
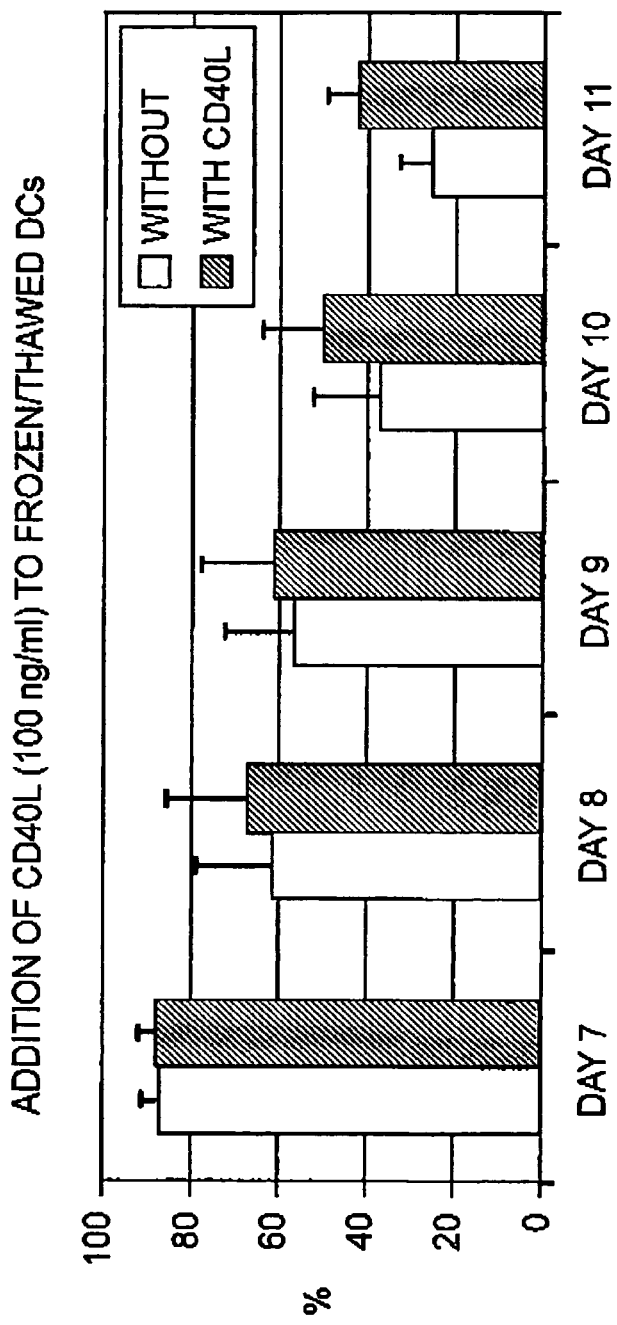
FIG. 9 shows that a contact with CD40L further improves the survival rate of thawed DCs. Mature d7-DCs were prepared as described for FIG. 1. After thawing, soluble primary CD40L (100 ng/ml) was added for 4 hours, then the DCs were washed and cultured for several days in medium without cytokines ("wash-out test") as described in the legend for FIG. 3. The yields of living DCs (stated as the percentage of frozen DCs) were determined immediately (=d7) and after several days of culture (after 1 day=d8, after 2 days=d9, etc.). CD40L treatment of DCs yielded an improved survival rate, especially beyound day 2 of the further culture (p<0.01 on day 10 and day 11; n=5).

A brief exposure of thawed DCs to the anti-apoptotic stimulants was as effective as the DC treatment prior to freezing and gave an increased survival rate, which often became visible only after 3 days in the "wash-out test", however. CD40L (FIG. 9) and TRANCE/RANKL (results not shown) yielded similar results. The results show that the addition of CD40L or TRANCE/RANKL improves the survival rate of DCs beyond day 3.

Example 5

In order to examine whether DCs can be successfully loaded with antigen prior to freezing, DCs were loaded with tetanus toxoid (TT) (as an example of a protein antigen) or with IMP (as a model peptide). For pulsing with TT, DCs were prepared from fresh or frozen aliquots of PBMCs from leucapheresis products (see above). TT was added to the immature cells on day 5 at 10 µg/ml. Mature DCs were harvested on day 7 and, either non-frozen or after freezing and thawing (after 4 h), examined for their capability of inducing TT-specific proliferative responses in PBMCs. Thus, graded doses of unpulsed and TT-pulsed DCs were added to PBMCs ($10 \times 10^4$/well) and pulsed with $^3$H-thymidine on day 5 as described (Thurner et al. (1999) *J. Immunol. Methods* 223, 1). For loading with IMP, DCs were pulsed with 10 µM peptide (for 1 h, 37° C., $1 \times 10^6$ DCs/ml of complete medium) either prior to freezing or after thawing. The capability of successfully presenting IMP was tested as described above.

Figure 10:
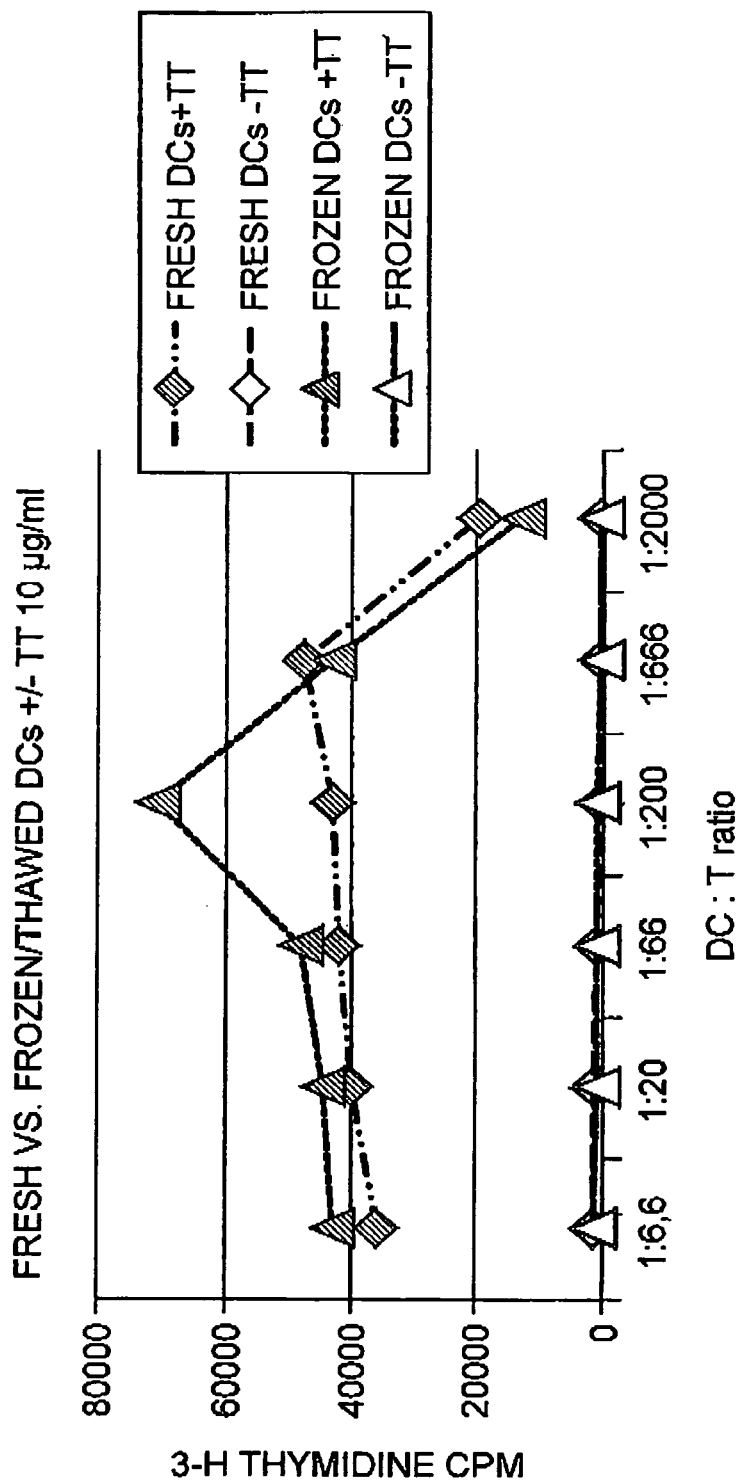
FIG. 10 shows that DCs can be successfully loaded with protein antigen prior to freezing. DCs were pulsed in their immature stage by adding the model antigen tetanus toxoid (TT) (10 μg/ml) on day 6. Mature DCs were then harvested on day 7 and frozen as described in the legend for FIG. 3. Frozen TT-pulsed DCs were stimulatory like freshly prepared TT-pulsed mature DCs.
Figure 11:
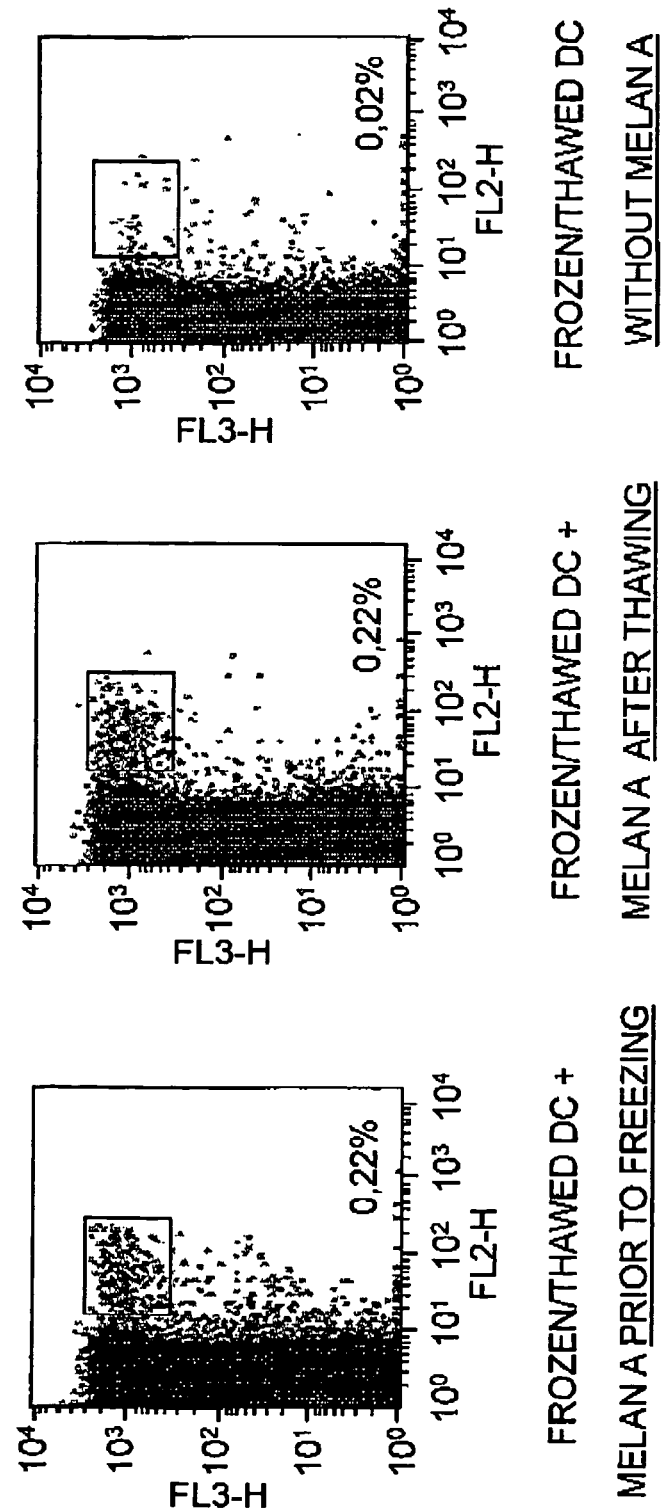
FIG. 11 shows that DCs can be successfully loaded with protein antigen prior to freezing. Frozen/thawed (see FIG. 3) HLA-A2.1+ mature d7 DCs were loaded with Melan-A-analogue peptide ELAGIGILTV (SEQ ID NO: 2) either prior to freezing or after thawing or left untreated and co-cultured for 7 days with autologous non-adherent fractions of PBMCs (PBMC:DC ratio-20:1) without adding any cytokines, harvested and double-stained with HLA-A2.1/Melan-A tetramers (X axis) and anti-CD8 (Y axis). The expansion of Melan-A-peptide-specific CD8+ T cells (the percentage of tetramer-binding CD8+ T cells is stated in the Figure) is comparable for frozen DCs which had been loaded prior to freezing or after thawing. See also FIG. 8.

Frozen TT-pulsed DCs had the same stimulatory properties as freshly prepared TT-pulsed DCs (FIG. 10). Both DCs loaded with IMP or Melan A prior to freezing and those loaded after thawing stimulated IMP- or Melan-A-specific CTLs equally well (FIGS. 8 and 11). These results show that it is possible to prepare frozen aliquots of mature DCs which have already been loaded with antigen and can be used immediately after thawing.

Example 6

Figure 12:
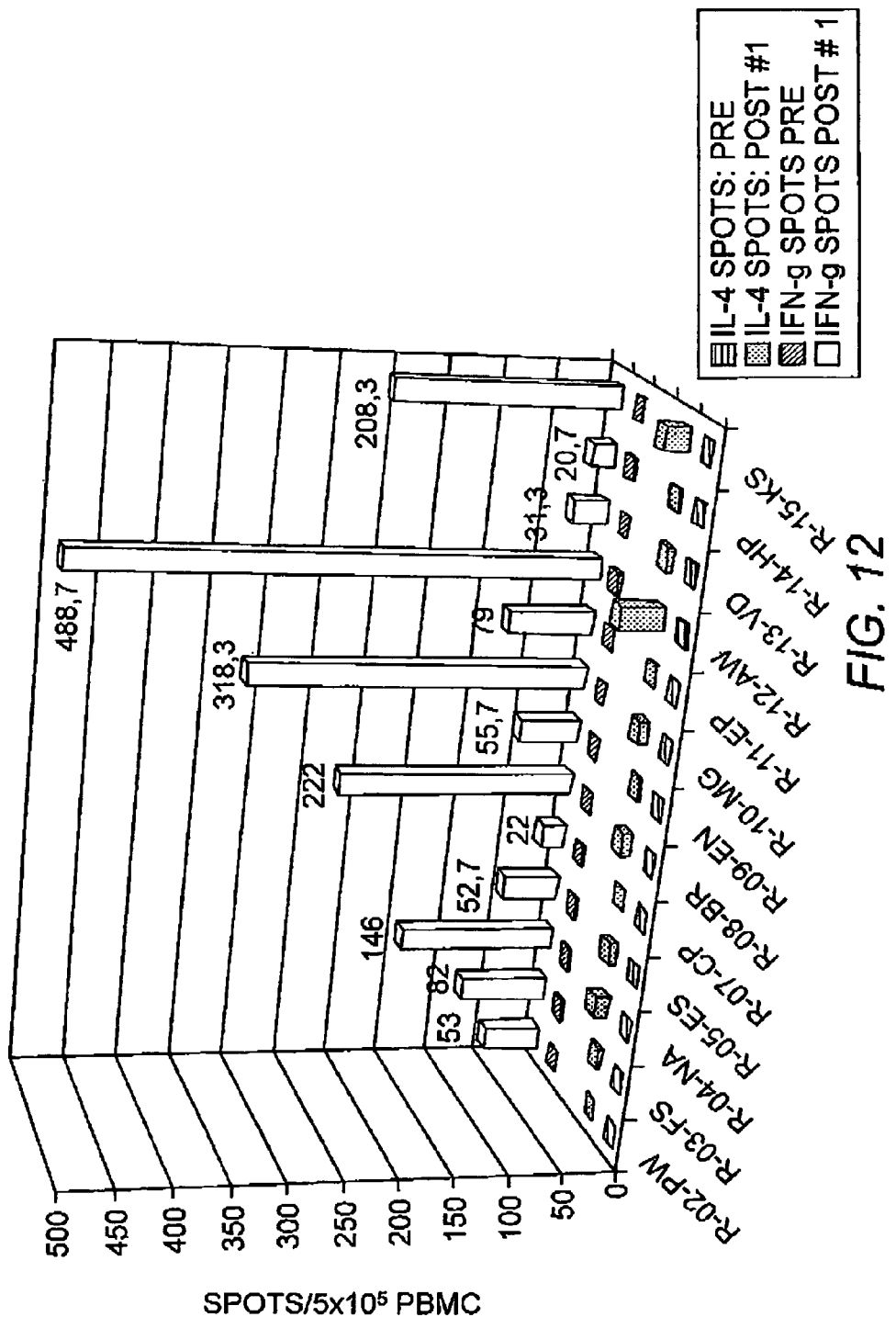
FIG. 12 shows the induction of a helper cell type 1 response against KLH in patients who were vaccinated as described in Example 6.

With stage IV melanoma patients, a vaccination was performed with peptide- and protein-loaded DCs prepared and antigen-loaded according to the method shown herein. FIG. 12 shows the induction of a helper cell type 1 response against KLH in all vaccinated patients. Each of the patients obtained a single subcutaneous delivery of 4 million mature DCs which had been prepared from leucapheresates using GM-CSF and interleukin-4 and the maturing composition as described in the application (e.g., FIGS. 1 and 3). In doing so, the control antigen KLH was added in a concentration of 10 µg/ml simultaneously with the maturing composition, and the DCs were then frozen in portions. Prior to vaccination and 14 days after said single administration of 4 million DCs, blood was removed and examined by a standard Elispot assay (addition of 10 µg/ml KLH to 500,000 PBMCs and measurement of the number of cells producing interferon-.gamma. or IL-4; the background without the addition of KLH is almost 0). It is found that neither interferon-γ nor interleukin-4 is produced upon KLH presentation prior to vaccination, whereas 14 days after the single vaccination with the KLH-loaded DCs, T cells which produced interferon-γ, but did not produce interleukin-4 or only minimally so were induced in all patients (in control experiments, it was shown by removing the CD4 cells from the PBMCs that the reactive cells are CD4-positive helper T cells).

Example 7

Figure 13:
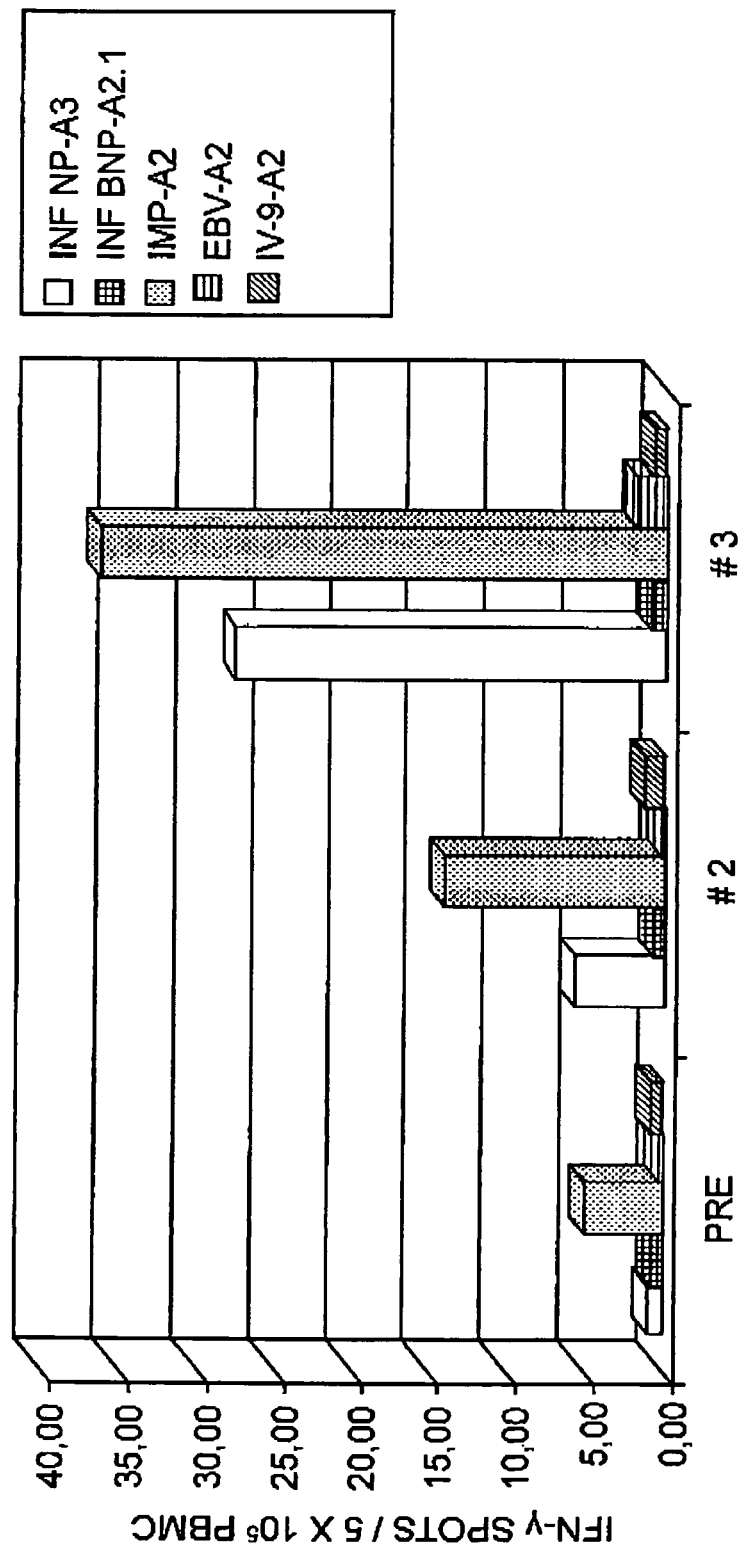
FIGS. 13-15 show the results of Example 7.
Figure 14:
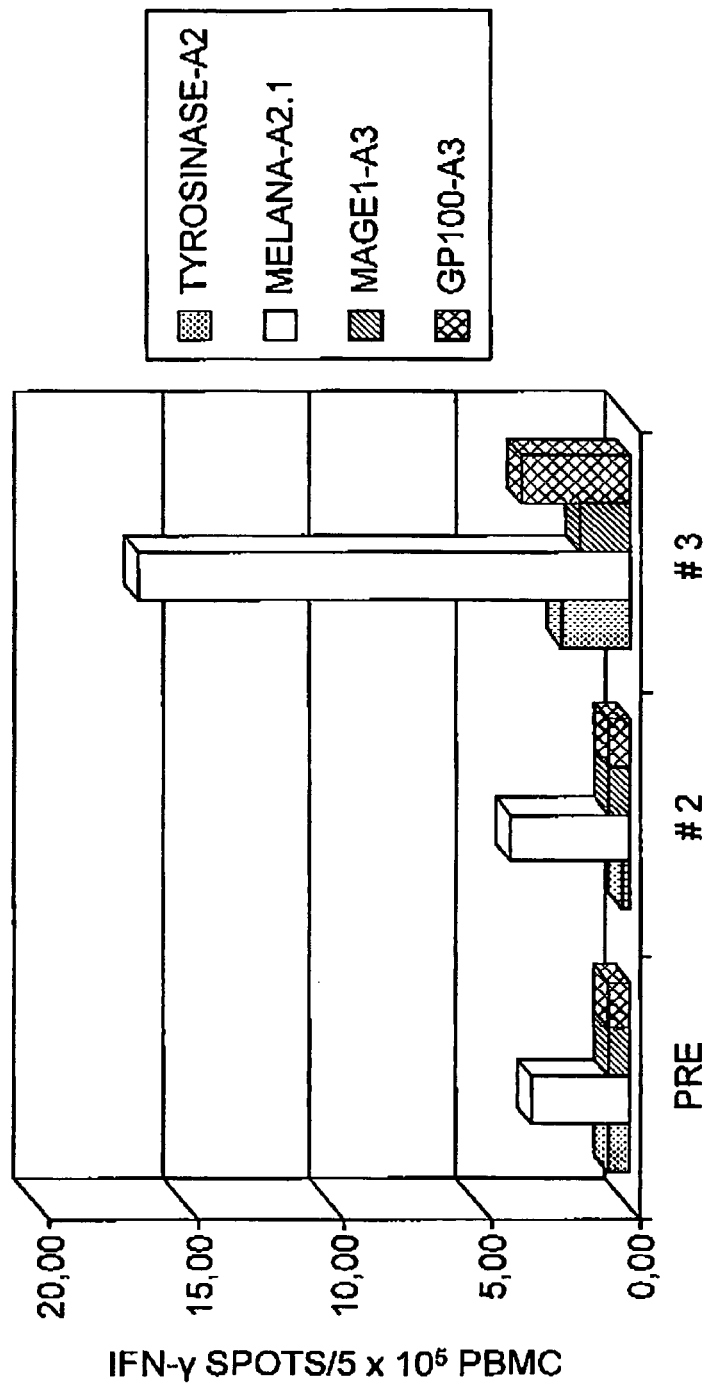
Figure 15:
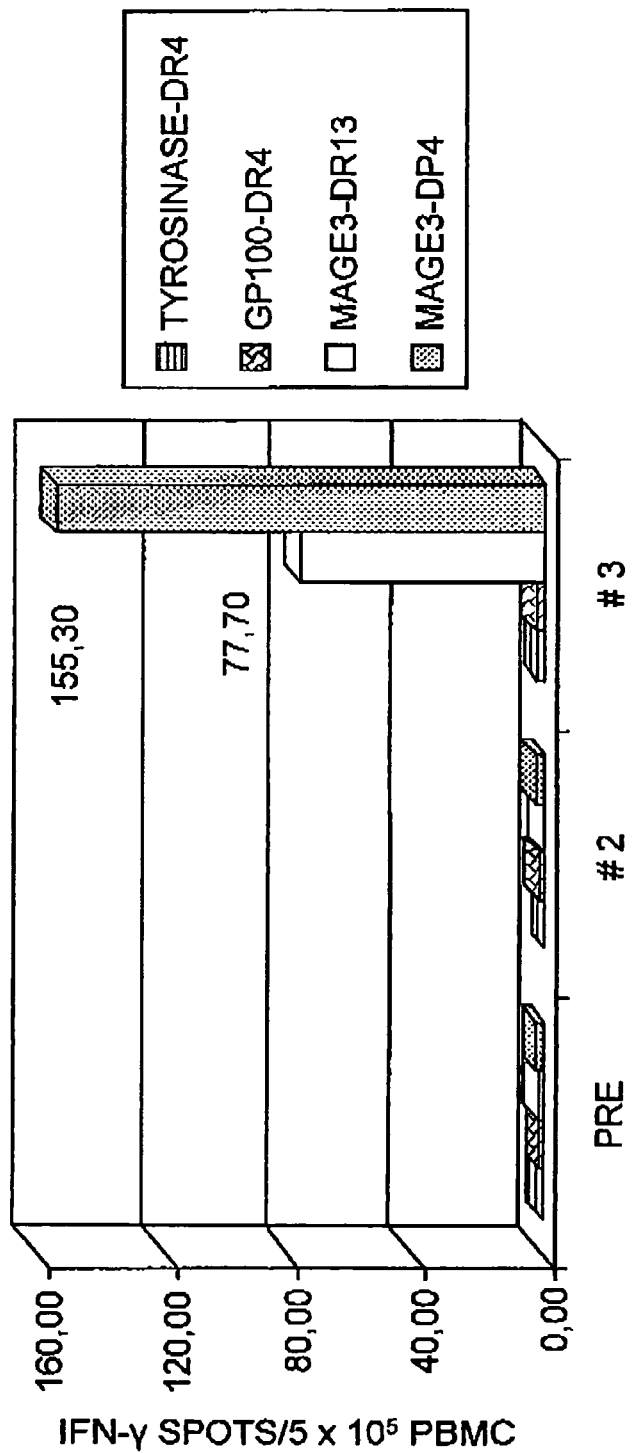

A patient from the study of Example 6 received several vaccinations with DCs, in which 4 million each of rethawed DCs were loaded with the peptides stated in FIG. 13, 14 or 15 (i.e., only 1 peptide respectively per 4 million DCs) and injected subcutaneously. Respectively prior to the first vaccination and 14 days after the respectively preceding vaccination and immediately before the next vaccination, blood was removed, and a standard Elispot assay was performed as described in Thurner et al. (1999), *J. Exp. Med.* 190, 1669-1678, under Materials and Methods. The DCs used for the vaccination were prepared as stated in the legend for FIGS. 8 and 11 and in Example 5, and loaded with the respective peptides only after thawing. As can be seen from FIGS. 13 to 15, immunity against several class-I (FIGS. 13 and 14) and class-II peptides (FIG. 15) was induced. The characteristics of the peptides employed can be seen from Table I. It is to be noted that the HLA type of the particular patient is HLA-A 2.1+ and HLA-A3+ as well as HLA-DR 13+, HLA-DP4+ (but DR4−). FIG. 13 shows the induction of immunity against the influenza peptides NP-A3 and IMP-A2 upon a single vaccination (No. 2 means the removal of blood and Elispot measurement briefly before the administration of vaccination No. 2) and shows an increase after another vaccination, but no change in EBV-A2 and IV-9-A2 peptides, which were not used for vaccination. FIG. 14 shows an induction of immunity against four class-I restricted tumor peptides, clearly and unambiguously against the peptide Melan A-A2.1. FIG. 15 shows an induction of immunity against two class-II restricted tumor peptides (Mage 3-DR13 and -DP4) but not against tyrosinase-DR4 and GP 100 DR4 (this is a negative control since the patient was DR4-negative, and the DCs thus could not be loaded with these peptides).

Example 8

Cryoconservation of Dendritic Cells after Antigen Loading with Tumor Cell Preparations (Tumor Cell Lysates, Necrotic or Apoptotic Tumor Cells)

Dendritic cells (DCs) can be generated in large amounts from leucaphereses. A method for the cryoconservation of mature DCs has been developed which allows the portioned use of these cells for vaccination. To date, the mature DCs were loaded prior to use with peptides which correspond to the immunodominant sequences of tumor-associated antigens (TAA). In the experiments described here (see FIG. 16), it was examined whether immature DCs which were loaded with different tumor cell preparations and subsequently matured can also be cryoconserved.

Tumor cell preparation: For preparing the tumor cell preparations, the Mel526 melanoma cell line was used. Mel526 cells were washed in RPMI and treated by repeated heatings at 57° C. and subsequent coolings in liquid nitrogen. Then, the cell material was disrupted by means of an ultrasonic device. Since the heating/freezing cycles induce necrosis, this kind of tumor cell preparation which contains all cell components is referred to as necrotic cell material in the following. For obtaining lysate, we performed an ultracentrifugation after these steps to remove cell components and effected purification of the proteins in a Centricon centrifugation tube. According to the results of the Bradford analysis, we used the protein fraction having the higher activity, namely that of ≥10 kDa. Apoptotic tumor cells were induced with a broad-range UVB irradiation device and verified with an Annexin V Test.

Generation of DCs: DCs were generated from leucaphereses according to the technique used in experimental immunotherapy. PBMCs were plated in Nunc Cell Factories and cultured with RPMI (1% autologous heat-inactivated plasma) supplemented with 1000 IU/ml GM-CSF and 500 IU/ml IL-4. On day 5, the DCs, which were immature then, were used and loaded for 4 hours with the tumor cell preparations described in a concentration of 1:1.

Loading: The loading was effected in a 5 ml polypropylene reaction vessel at 37° C. and 5% $CO_2$. After the loading, the DCs were plated in 12 ml tissue culture dishes and cultured with a maturing cocktail consisting of TNF-α, IL-1β, IL-6 and $PGE_2$ for 24 h.

Freezing/thawing: Half of the respectively loaded DCs were respectively cryoconserved in 1.8 ml Nunc freeze vials at −80° C. for 3 hours according to the method described (Feuerstein et al., *J. Immunol. Methods* 245: 15-29 (2000)). Thereafter, the cells were again thawed according to the method described and cultured for one hour in RPMI medium at 37° C. and 5% $CO_2$. Subsequently, this fraction of the DCs as well as the non-frozen fraction were analyzed and used for further experiments.

Figure 16:
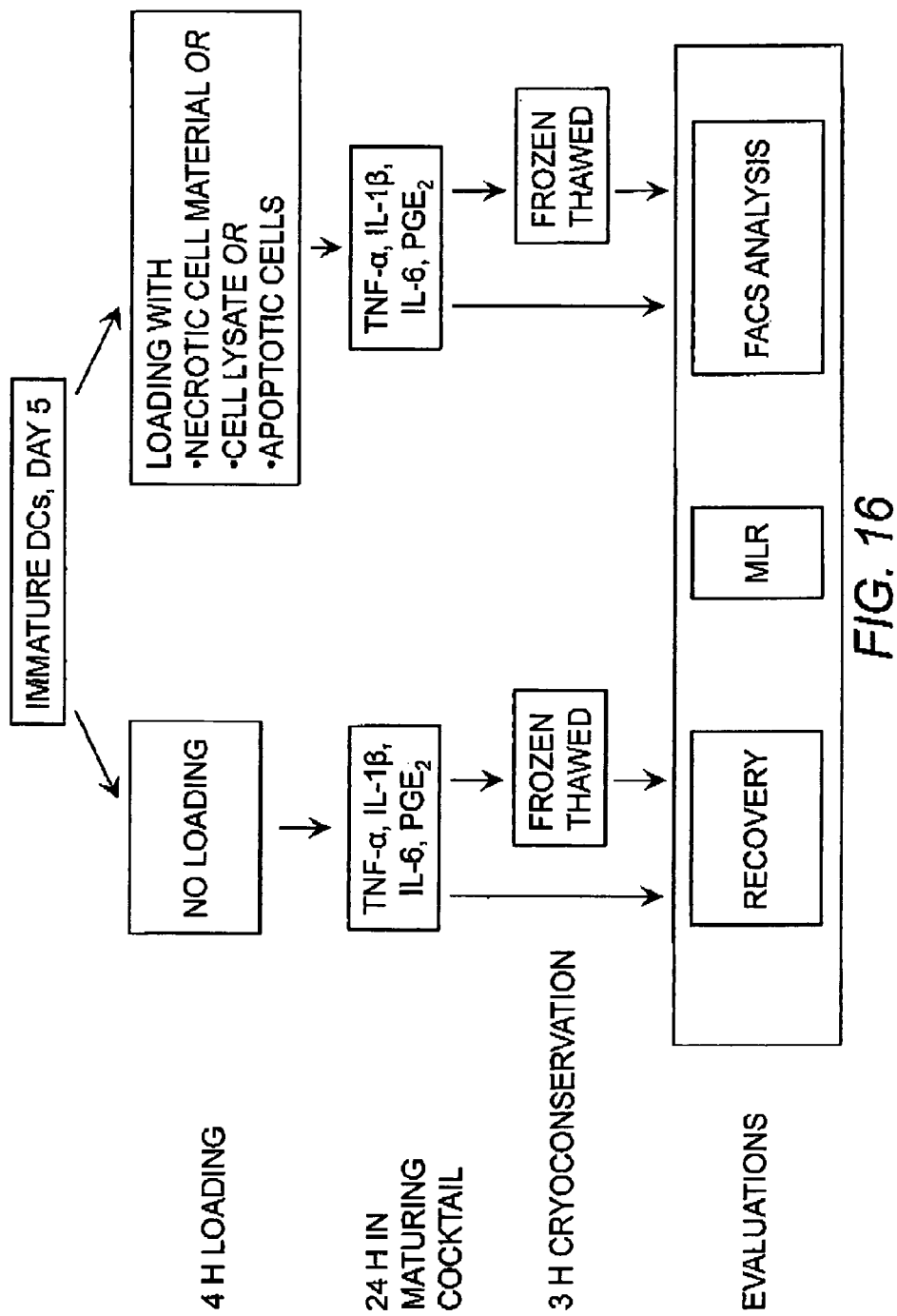
FIG. 16 shows a schematic representation of the experimental set-up of Example 8. The results of Example 8 are summarized in FIGS. 17 and 18.

The experimental set-up described is shown as a flow chart in FIG. 16.

Figure 17A:
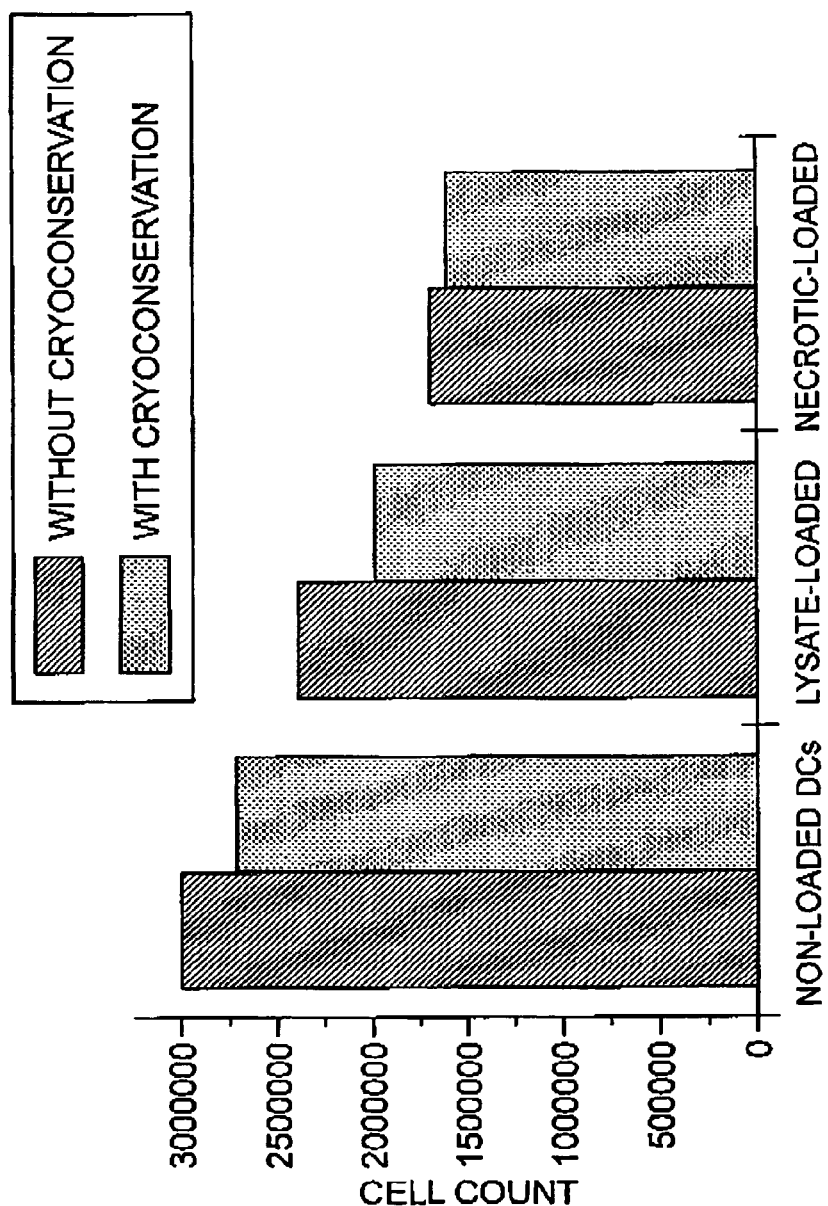
FIG. 17A shows the total number of DCs after loading with tumor cell lysate or necrotic tumor cells and subsequent cryoconservation.

Cell count and viability: The total cell count and viability of the DCs were determined with trypan blue with a microscope after performance of the loading described and cryoconservation. Initially, $5 \times 10^5$ DCs were used. We found comparable cell counts and no difference in the viability of the loaded and cryoconserved DCs as compared with the non-cryoconserved cells (FIGS. 17A, 18A). A reduction of the cell count by the loading, but not by the cryoconservation, especially with necrotic cells, could be observed.

Figure 17B:
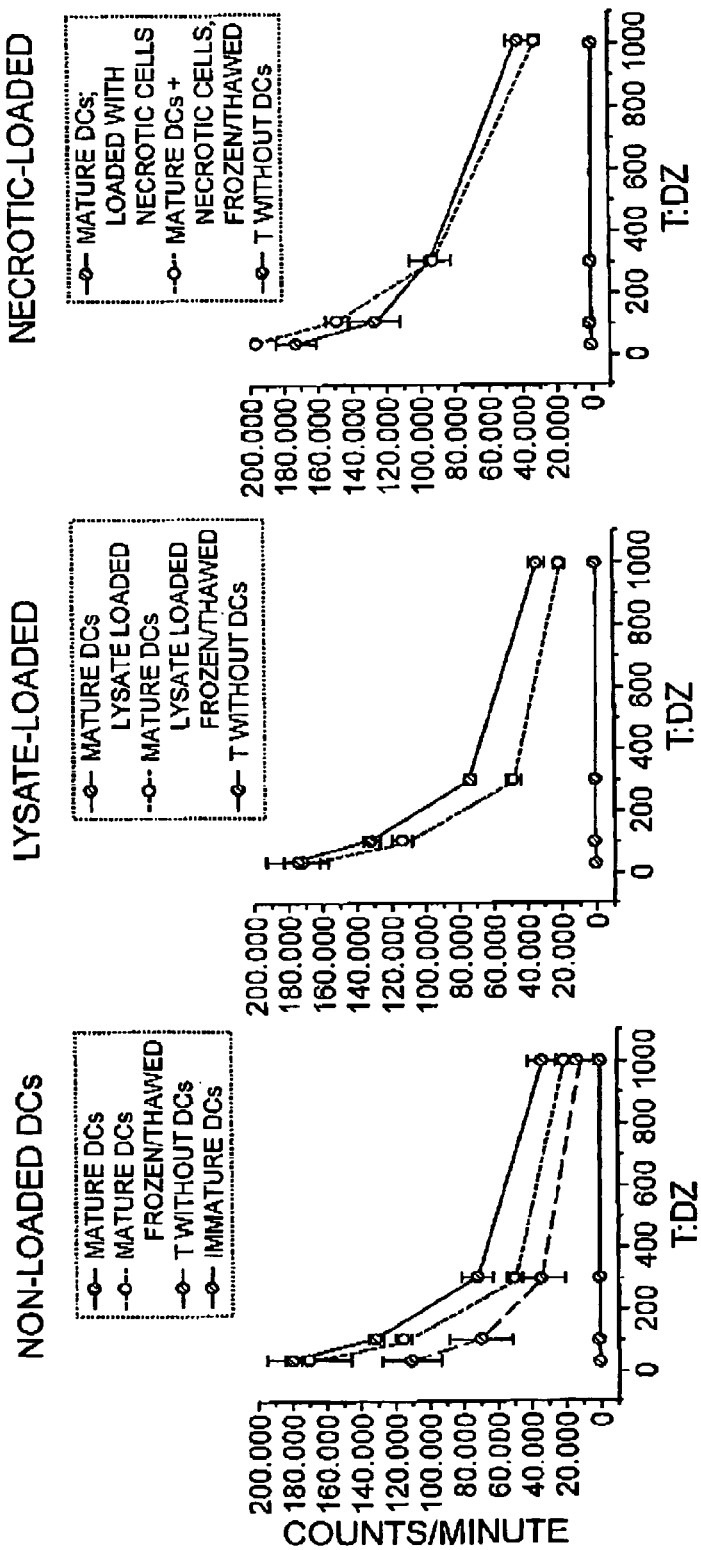
FIG. 17B shows the allostimulatory potency of DCs after loading with tumor cell lysate or necrotic tumor cells and subsequent cryoconservation.
Figure 18B:
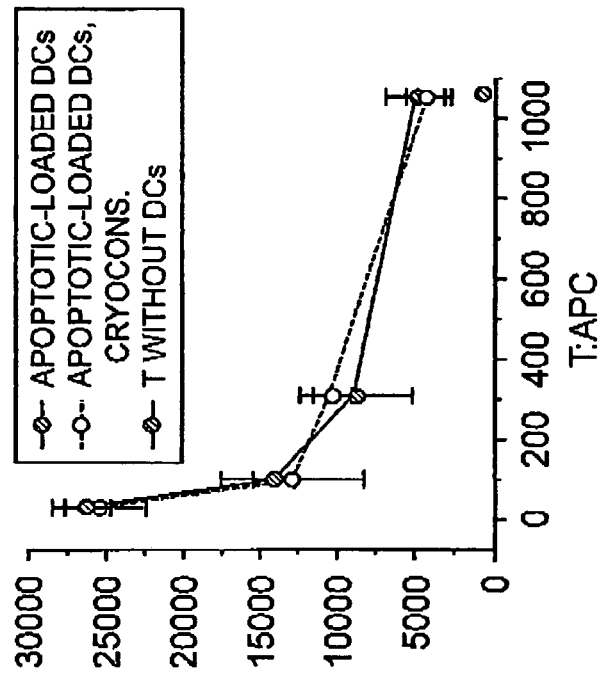
FIG. 18B shows the allostimulatory potency of DCs after loading with apoptotic MEL 526 melanoma cells and subsequent cryoconservation.
Figure 18B:
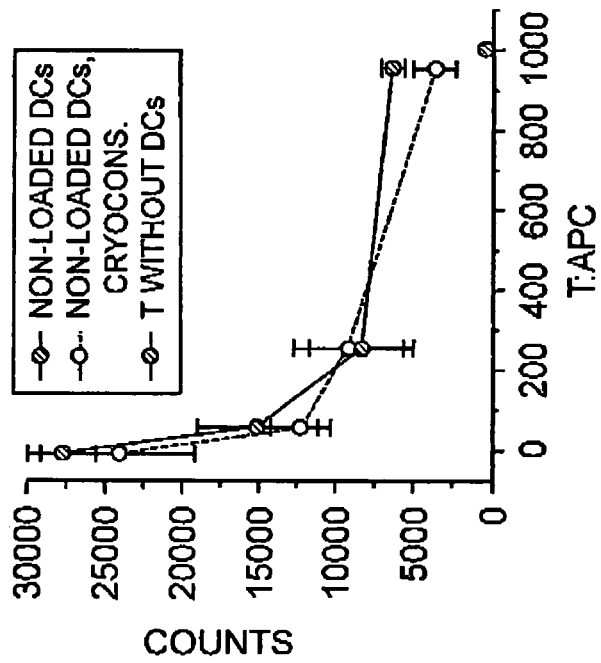

Functionality: For testing the functional capacity, a mixed-leucocyte reaction test (MLR) was performed. The loaded DCs were employed in an allogenic MLR (4 days of incubation with allogenic leucocytes) and then pulsed with radioactive thymidine ($^3$H-thymidine) for 13 hours. Comparable allostimulatory potencies were obtained for cryoconserved and non-cryoconserved loaded DCs (FIGS. 17B, 18B).

Figure 17C:
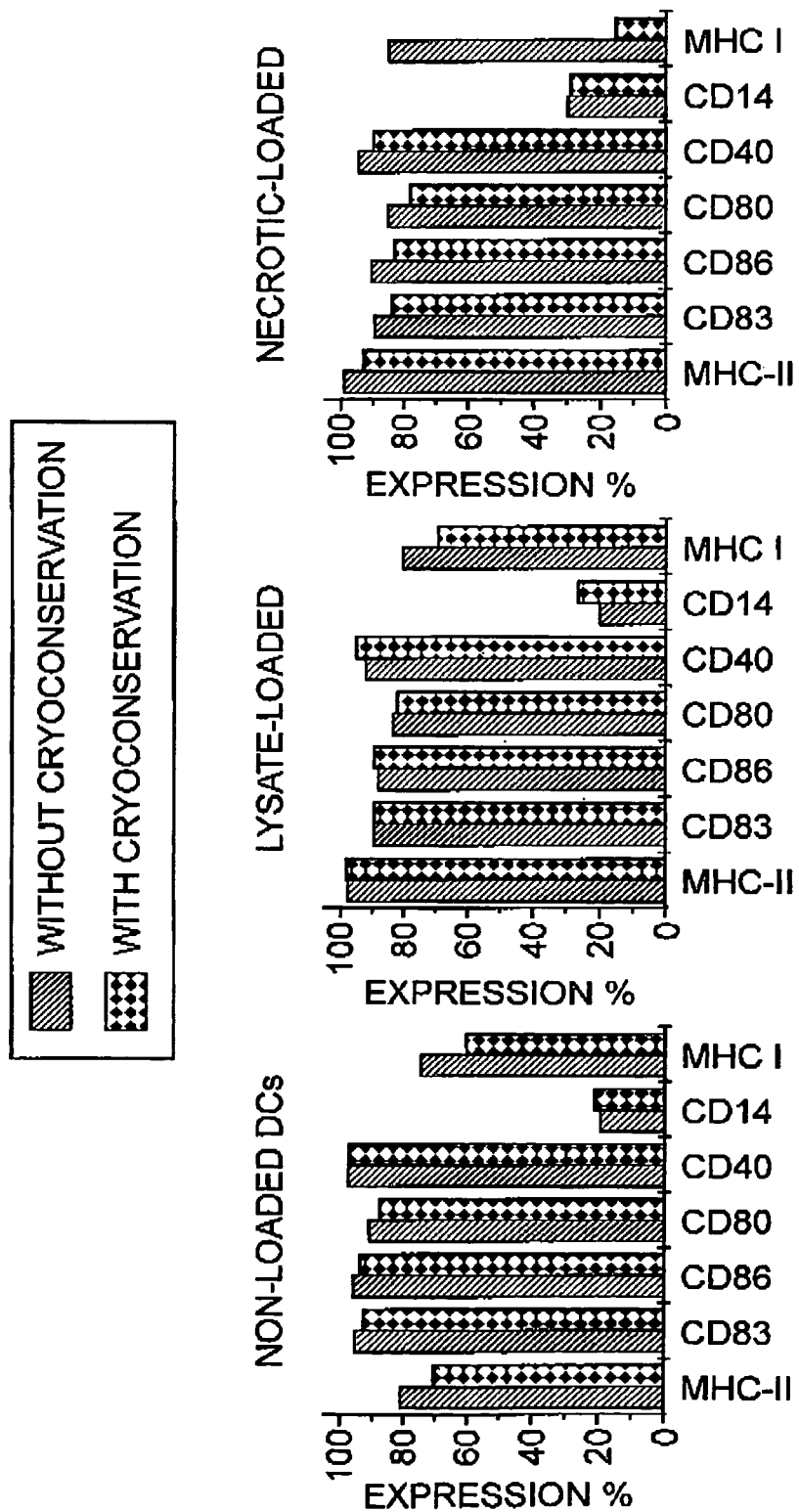
FIG. 17C shows the result of the FACS analysis after tumor loading and cryoconservation.

Phenotype: For evaluating the expression of the surface molecules relevant to antigen presentation and the functional condition of the DCs, a FACS analysis was performed with the corresponding antibodies. A comparable surface expression pattern was found both for the different loading methods and after cryoconservation (FIG. 17C).

Figure 18C:
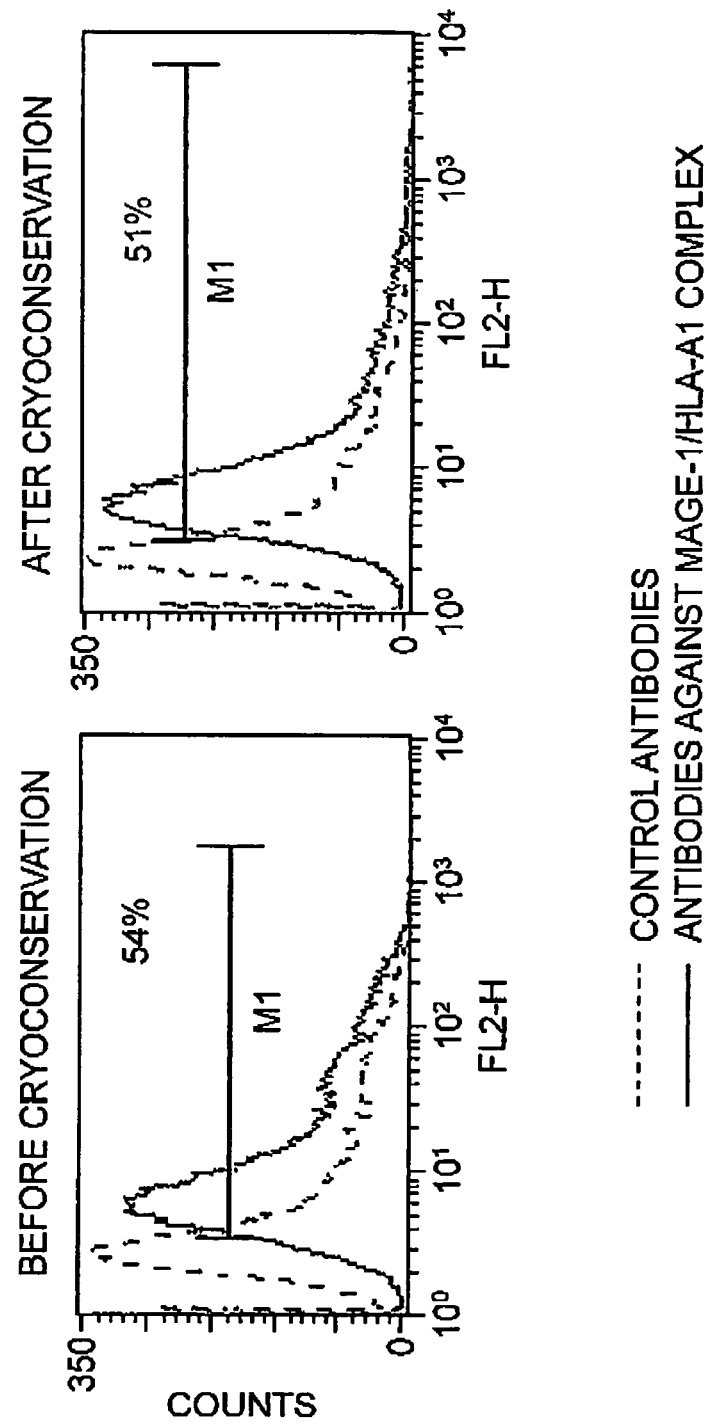
FIG. 18C shows the results of the FACS analysis of MAGE-1/HLA-A1 Ag expression on Mage-1 peptide-pulsed DCs prior to and after cryoconservation.

Direct antigen detection: For the direct detection of tumoral antigen, an antibody was employed which recognizes MAGE-1 in an HLA-A1 context, i.e., the complex of Mage-1 peptide and the HLA-A1 molecule. The differently loaded DCs were dyed with this antibody and analyzed in the FACS. When peptide-loaded (20 μg MAGE-1 peptide for 3 hours/ml) DCs were used, it was found that after cryoconservation, a percentage of MAGE-1/A1 antigen could be detected which was comparable to that detected without cryoconservation (FIG. 18C). From this experiment, it can be concluded that the cryoconservation does not lead to a loss in antigen.

Figure 18D:
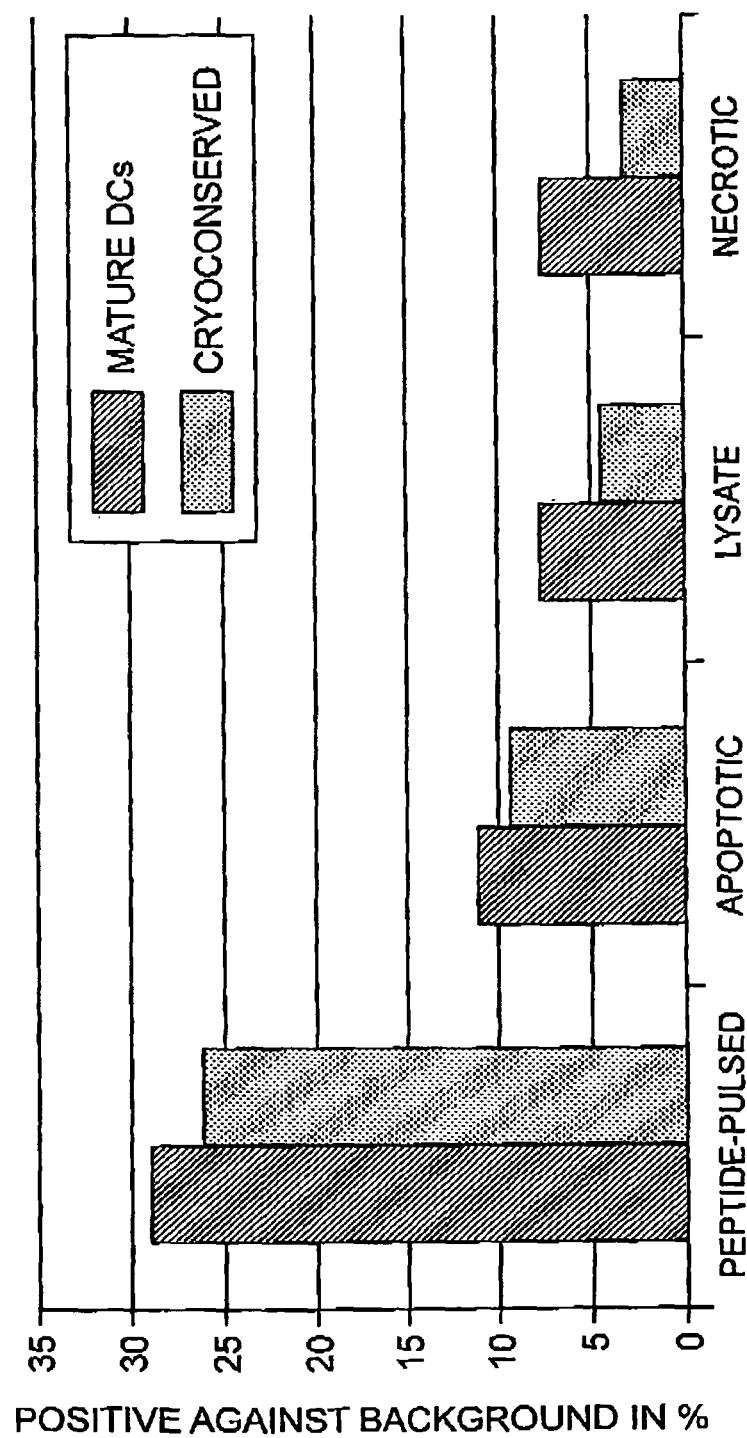
FIG. 18D shows a comparison of the expression of MAGE-1/HLA-A1 complexes (determined by means of antibodies against MAGE-1/HLA-A1 complex) prior to and after cryoconservation on DCs which had been loaded in different ways.
Figure 19:
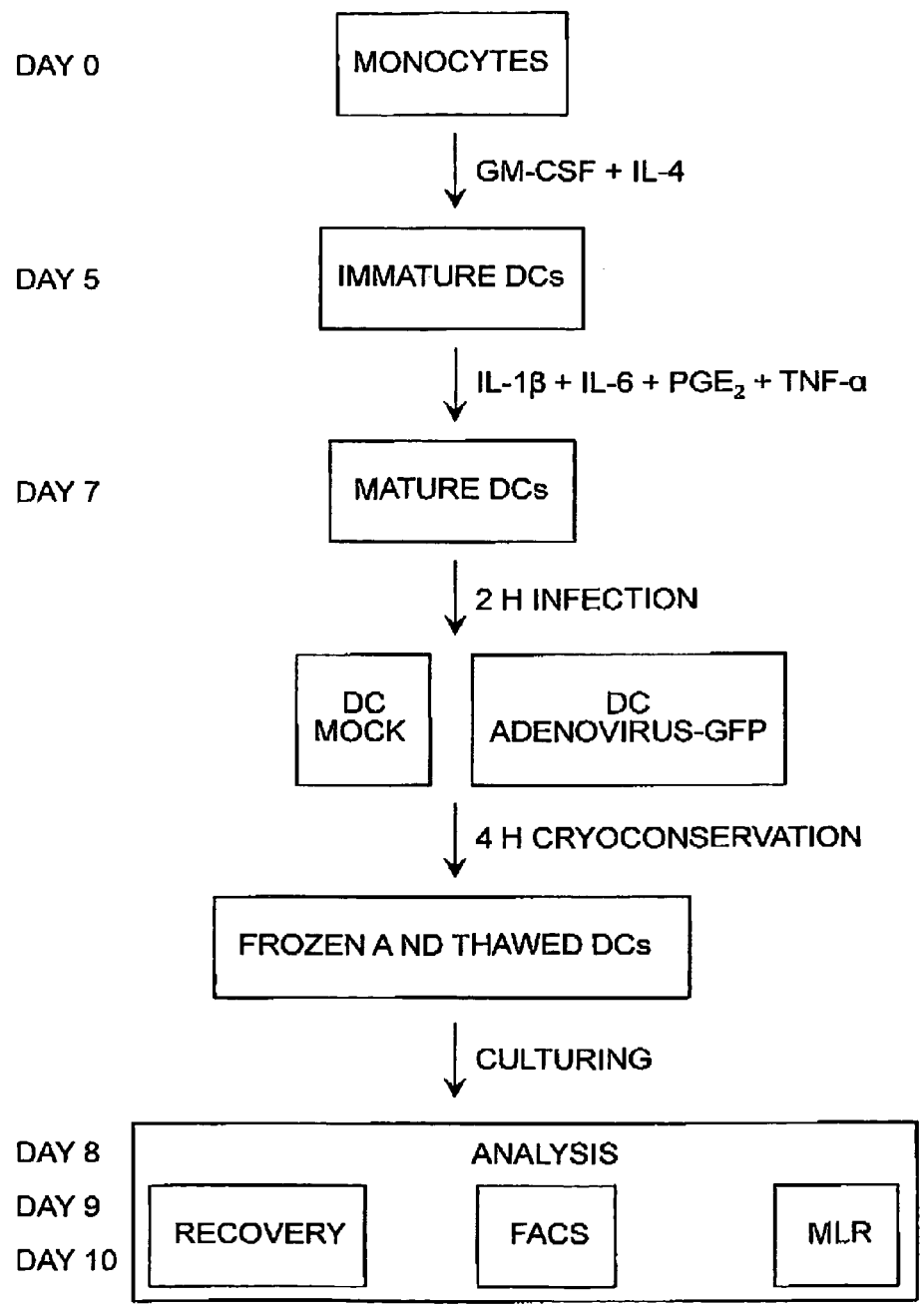
FIG. 19 shows a schematic representation of the experimental set-up of Example 9 in which adenovirus-infected dendritic cells with or without cryoconservation are compared. The results of Example 9 are summarized in FIGS. 20 to 23.

In a further experiment, the MAGE-1/A1 antibody was employed for determining the effectiveness of the different loading methods. With the tumor cell preparations (the melanoma cell line employed expresses the Mage-1-antigen), a significant loading could be achieved which reached about 20% of the antigen density of the peptide pulsing (FIG. 18D). The expression of the MAGE-1/HLA-A1 complex before and after the cryoconservation could be detected in comparable quantities (calculated as positivity against the background of unloaded DCs).

Conclusion: It could also be shown that the method of the present invention allows not only an effective cryoconservation of unloaded DCs or DCs loaded with peptide or protein (as shown in Examples 1-7), but also a similarly effective cryoconservation of DCs loaded with (tumor) cell preparations (simple necrotic tumor cells, lysates prepared from tumor cells, or apoptotic tumor cells). "Effectively" means that upon freezing, i) the cell loss after thawing is ≤25% as compared with non-frozen DCs, ii) the thawed DCs have a T cell stimulatory capacity comparable to that of the non-frozen DCs (tested in allogenic MLR), and iii) the surface expression of antigens and ligands for T cell receptors (i.e., specific MHC peptide complexes) is retained after the freezing and thawing process (shown in a model by the direct detection of a particular peptide/MHC complex, namely the MAGE-1/HLA-A1 complex, by means of a monoclonal antibody which specifically recognizes this complex).

Example 9

Cryoconservation of Dendritic Cells after Antigen Loading by Means of Adenoviral Transfection Dendritic cells transfected with adenoviruses can be frozen by the method according to the invention in such a way that the properties of the dendritic cells are comparable with those of non-transfected dendritic cells. For this purpose, mature DCs were infected with an adenoviral vector (AD5) which contained a cDNA coding for the green fluorescent protein (GFP) at a multiplicity of infection (MOI) of 500 for 2 hours.

Figure 20:
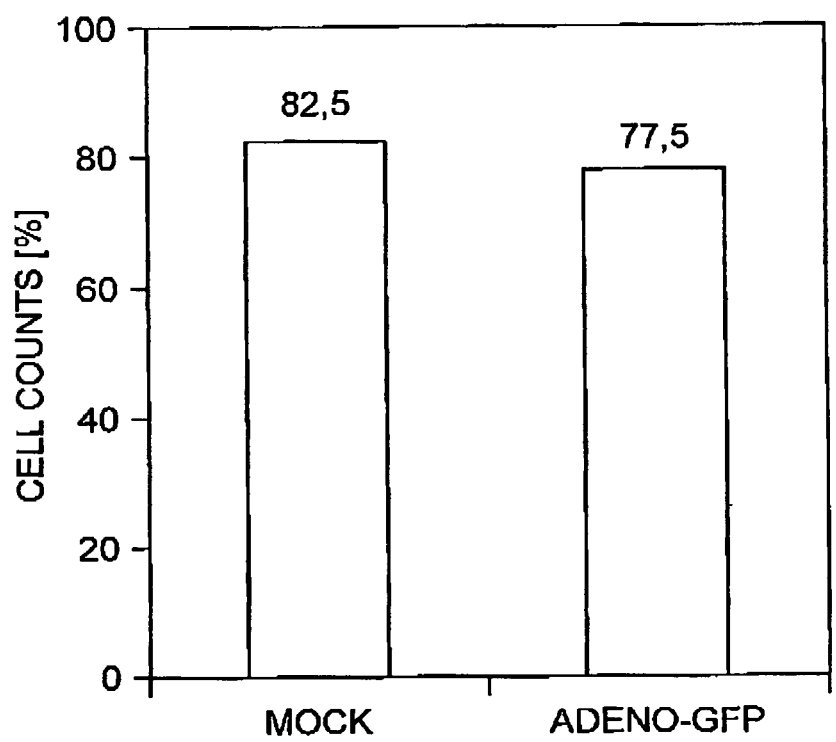
FIG. 20 shows the recovery of adenovirus-infected dendritic cells after cryoconservation. The recovery rate of adeno-GFP infected DCs after freezing and rethawing is comparable with that of mock-treated (non-transfected) DCs.

After two washes, the cells were frozen at a concentration of $10 \times 10^6$ DCs/ml in HSA and 10% DMSO in 5% glucose (final concentration) and stored for 4 hours. After thawing, the viability of the cells was determined by trypan blue exclusion. The recovery rate of viable cells is stated in FIG. 20 as a percentage of frozen DCs.

Figure 21:
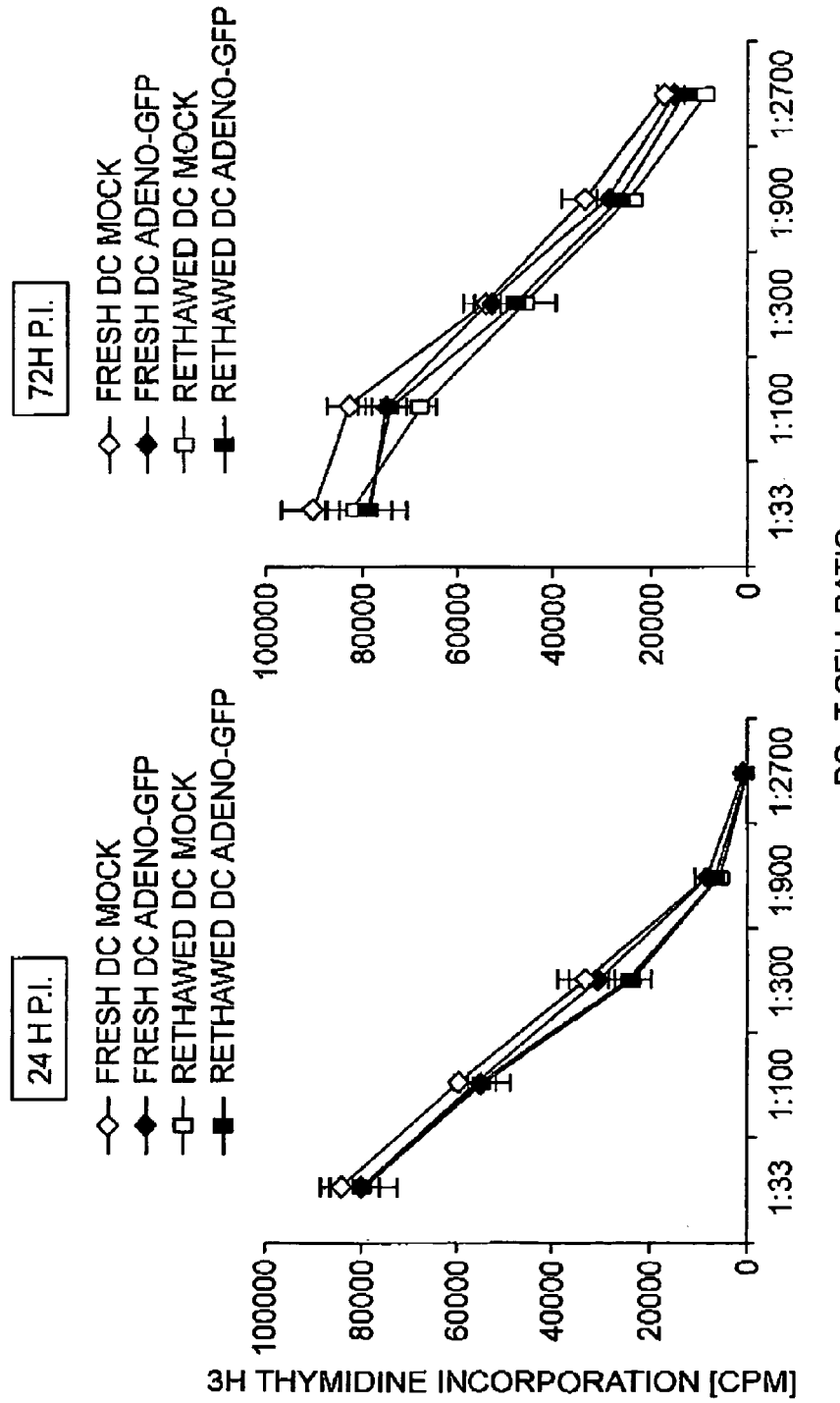
FIG. 21: CD4 T-cell stimulating activity of adenovirus-infected dendritic cells after cryoconservation. It can be shown that the cryoconservation does not change the allostimulatory activity of adenovirus-infected DCs.

Further, it could be shown that the allostimulatory activity of adenovirus-infected DCs is not changed by cryoconservation. Thus, mature DCs were infected with adeno-GFP at an MOI of 500 and cryoconserved as described above. After rethawing and a culturing period of 24 or 72 hours, the dendritic cells were co-cultured with allogenic CD4+ T cells ($2 \times 10^5$ per well) under the conditions stated in FIG. 21. After 4 days, the cells were pulsed with [$^3$H]-thymidine for 16 hours, and the incorporated radioactivity was determined. In FIG. 21, the average values of three counts are stated with the corresponding standard deviations. The values for T cells alone or DCs alone were always less than 1000 per min.

Figure 22A:
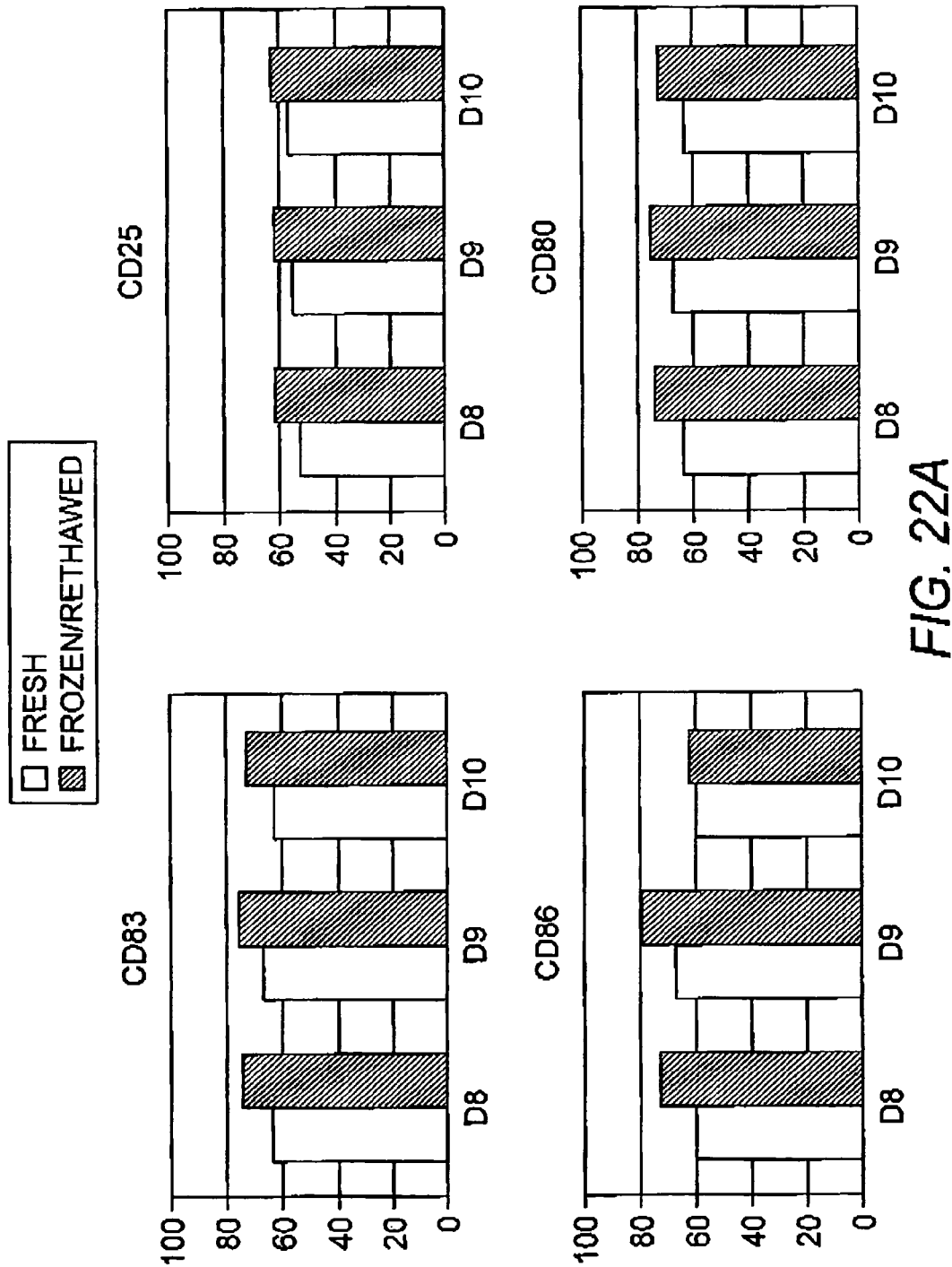
FIGS. 22A and 22B show that a similar phenotype is observed in adenovirus-infected DCs with or without cryoconservation.
Figure 22B:
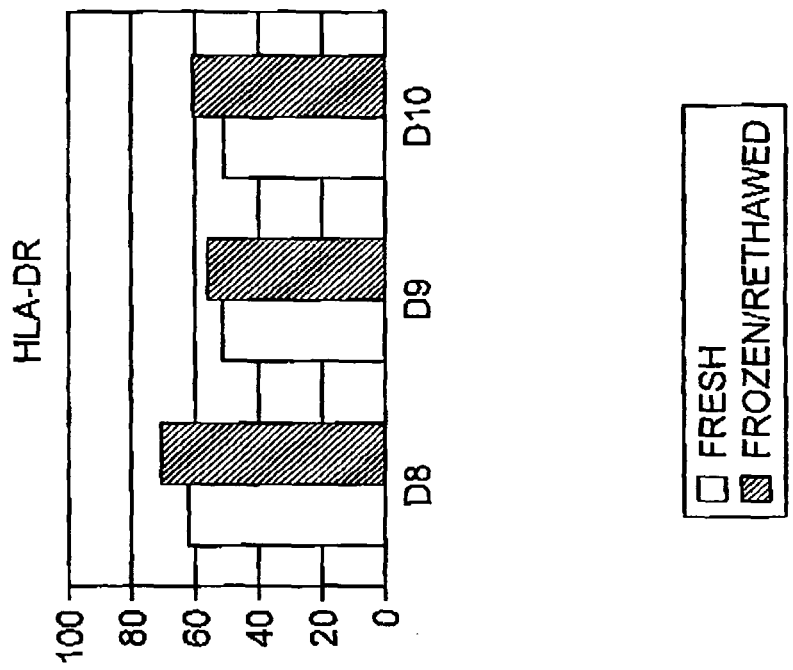
Figure 22B:
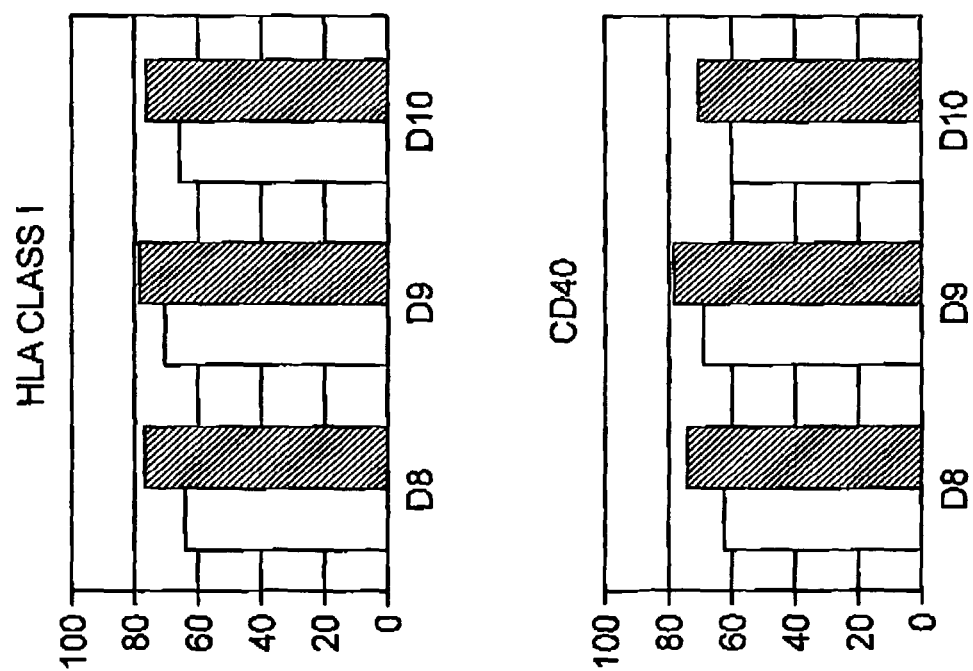
Figure 23A:
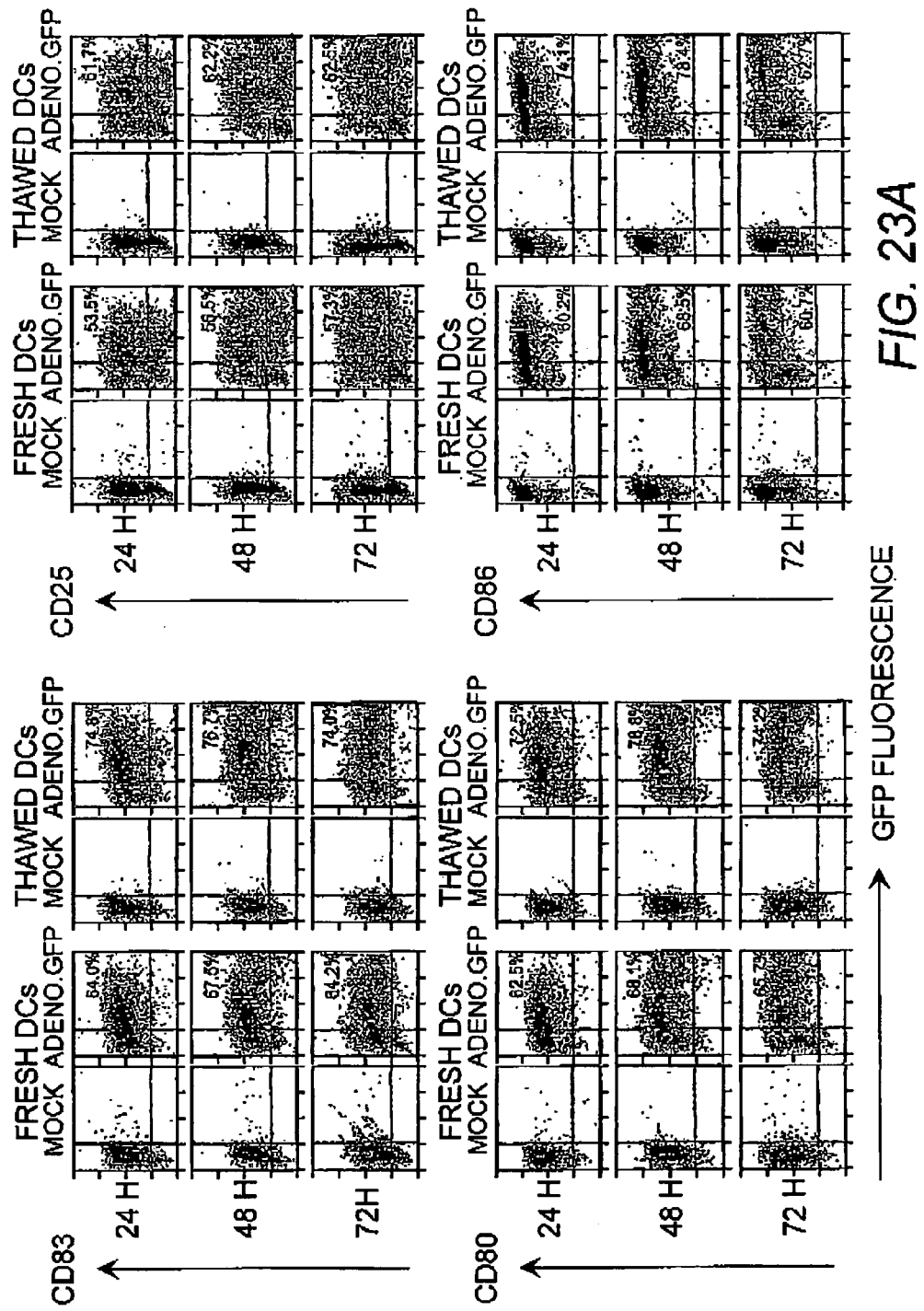
FIGS. 23A and 23B show a phenotype of adenovirus-infected DCs with or without cryoconservation.
Figure 23B:
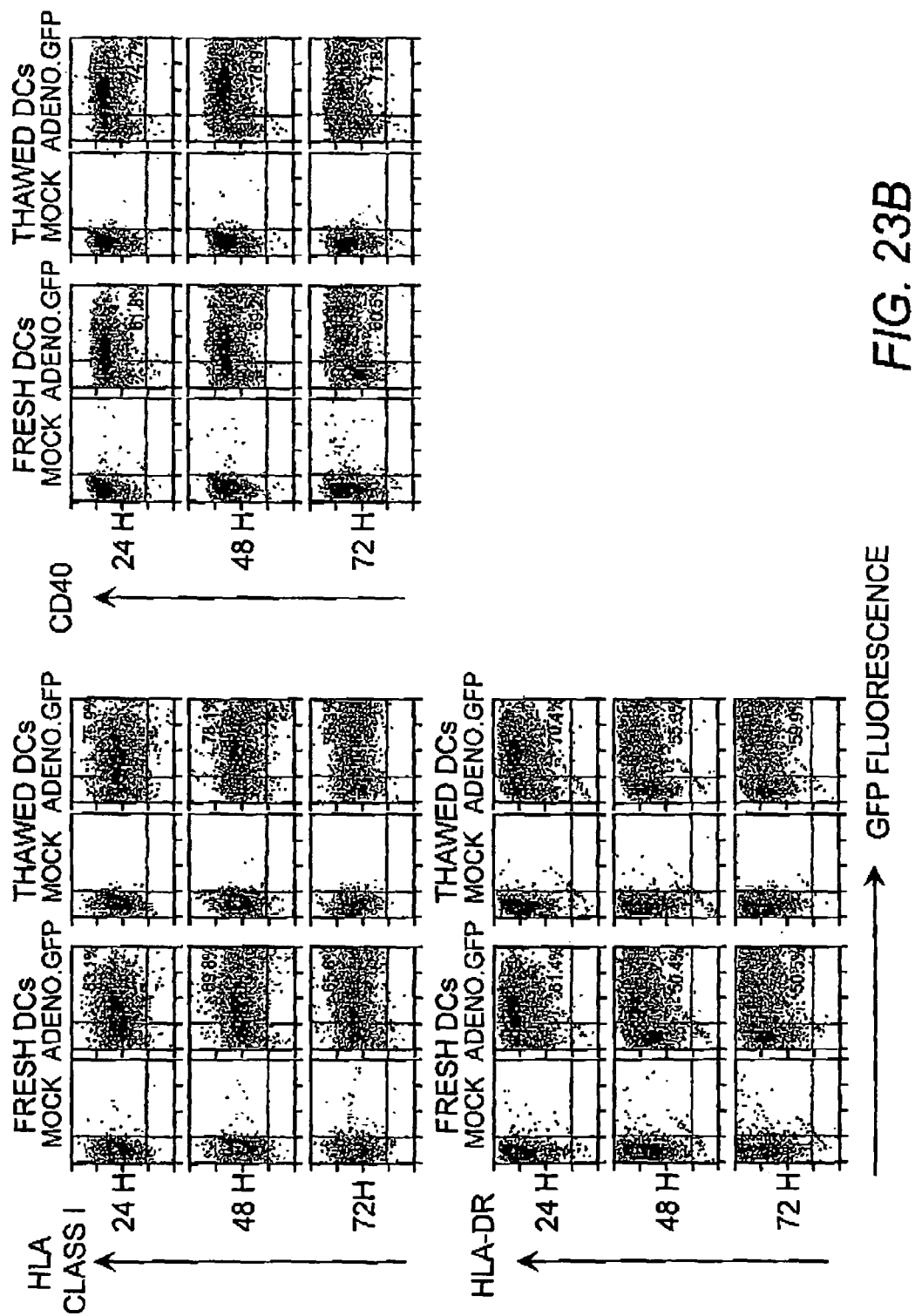
Figure 24:
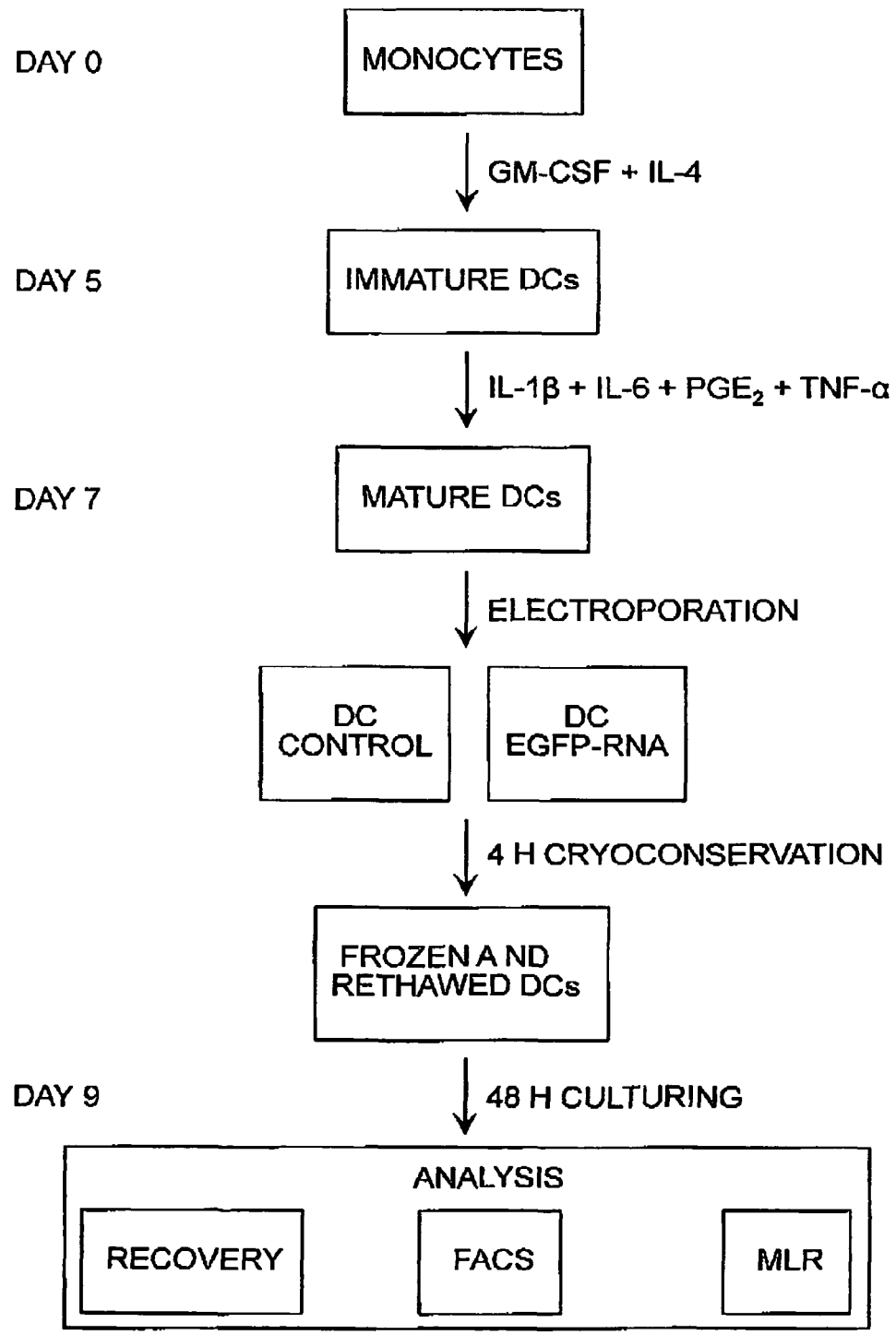
FIG. 24 shows the schematic course of the experiment of Example 10 as compared with RNA-electroporated DCs with or without cryoconservation. The results are summarized in FIGS. 25 to 27.

Further, mature DCs are cryoconserved with adeno-GFP at an MOI of 500 as described above. After rethawing and the stated culturing time, the cells were counterstained using antibodies specific for CD83, CD25, CD86, CD80 followed by PE-conjugated goat/mouse IG (Fab')$_2$ fragments. The results are shown in FIG. 22A. In a comparable experiment using antibodies specific for HLA class 1, HLA-DR and CD40, the results shown in FIG. 22B were obtained.

Example 10

Figure 25:
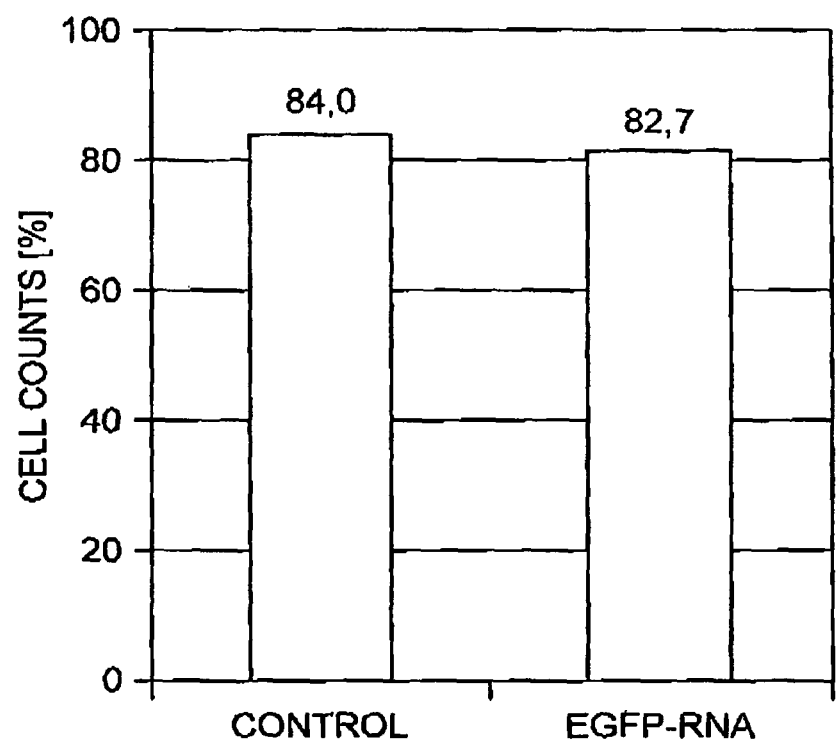
FIG. 25 shows that the recovery after cryoconservation of EGFP-RNA-electroporated DCs is similar to that in the control experiment.

Cryoconservation of Dendritic Cells after Antigen Loading by Means of RNA Transfection Dendritic cells transfected with RNA can be frozen by the method according to the invention in such a way that the properties of the dendritic cells are comparable with those of non-transfected dendritic cells. The DCs can be transfected with RNA in an immature stage, then matured, and then frozen as mature DCs (not shown). Preferably, DCs which are already mature are transfected with RNA and cryoconserved. The results are summarized in FIGS. 25 to 27.

Thus, mature dendritic cells were washed twice with RPMI and once in a washing solution of the Optimix kit (EQUI-BIO), Maidstone Kent, UK). DCs were brought to a final concentration of $40 \times 10^6$ DCs/ml in Optimix medium. Then, 0.1 ml of the cell suspension were mixed with 40 µg of in-vitro transcribed EGFP RNA in a 1.5 ml reaction vessel. After incubation at room temperature for a maximum of 3 min, the cell suspension was transferred into a 0.4 cm gap electroporation cuvette and pulsed at a voltage of 260 V and a capacitance of 150 µF with a Gene Pulser II (Biorad, Munich, Germany). Control DCs were pulsed without the addition of RNA. The cells were frozen at a concentration of $10 \times 10^6$ DCs/ml in HSA (with 10% DMSO and 50% glucose (final concentration)) and stored for 4 hours. After thawing, the viability of the cells was determined by trypan blue exclusion. The recovery rate of viable cells is stated in FIG. 25 as a percentage of frozen DCs.

Figure 26:
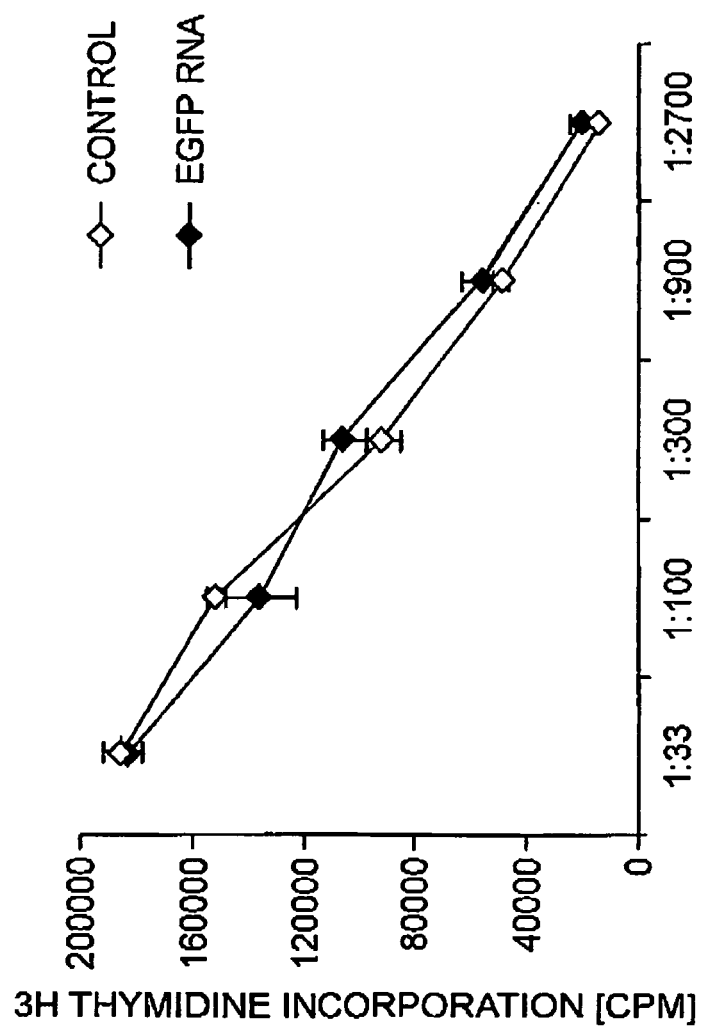
FIG. 26 shows that the cryoconservation does not change the allostimulatory capacity of EGFP-RNA-transfected DCs.
Figure 27:
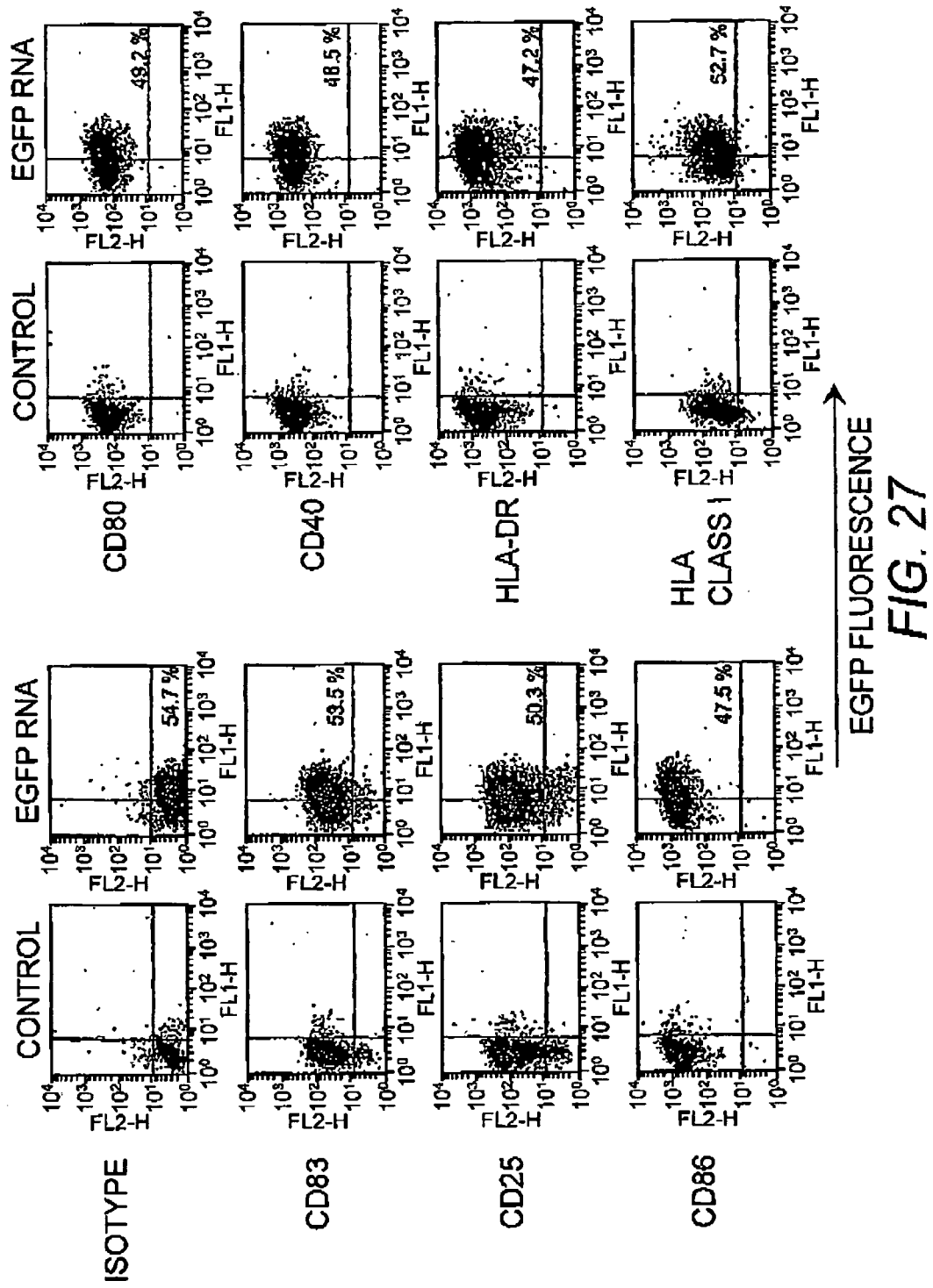
FIG. 27 shows that the phenotype of RNA-transfected DCs is similar to that in the control experiment.

Mature DCs were electroporated with EGFP RNA and cryoconserved as described above. After rethawing and a culturing period of 48 hours, the dendritic cells were co-cultured with allogenic CD4+ T cells ($2 \times 10^5$ per well) under the conditions stated in FIG. 26. After 4 days, the cells were pulsed with [$^3$H]-thymidine for 16 hours, and the incorporated radioactivity was determined. In FIG. 26, the average values for triplicate measurements (with standard deviation) are shown. The values for T cells alone or DCs alone were always less than 1000 per min.

The cryoconservation of RNA-electroporated DCs does not change the phenotypical DC marker. Thus, mature DCs were electroporated with or without EGFP RNA and cryoconserved as described above. After rethawing and a culturing time of 48 hours, the DCs were counterstained using the mouse monoclonal antibodies stated in FIG. 27 and PE-conjugated anti-mouse IG (Fab')$_2$ fragments, followed by FACS analysis. The figures in the right bottom portion of the square in FIG. 27 relate to the EGFP-positive DCs, and those in the top right portion relate to the EGFP/DC-marker double-positive DCs.

We claim:

1. Mature dendritic cells frozen in freezing medium comprising autologous serum, 5-25% DMSO, and 5-10% glucose.

2. The dendritic cells of claim 1, wherein said cells are frozen in said freezing medium at a concentration of from $5 \times 10^6$ cells/ml to $20 \times 10^6$ cells/ml.

3. The dendritic cells of claim 1, wherein said dendritic cells are antigen-loaded.

4. The dendritic cells of claim 3, wherein said dendritic cells are loaded with a DNA or RNA molecule which codes for said antigen.

5. The dendritic cells of claim 3, wherein said dendritic cells are loaded with an RNA molecule that codes for an antigen.

6. The dendritic cells of claim 1, wherein said cells are frozen in said freezing medium at a concentration of $10 \times 10^6$ cells/ml.

7. The dendritic cells of claim 1, wherein said freezing medium contains from 10% to 20% DMSO.

8. The dendritic cells of claim 1, wherein said dendritic cells are derived from monocytes.

9. The dendritic cells of claim 1, wherein said freezing medium contains from 10% to 20% DMSO and 5% glucose.

10. The dendritic cells of claim 1, wherein said dendritic cells are loaded with an RNA molecule that codes for an antigen and wherein said freezing medium contains 10% DMSO and 5% to 10% glucose.

* * * * *

SEQUENCE LISTING

<160> NUMBER OF SEQ ID NOS: 27

<210> SEQ ID NO 1
<211> LENGTH: 9
<212> TYPE: PRT
<213> ORGANISM: Influenza virus

<400> SEQUENCE: 1

Gly Ile Leu Gly Phe Val Phe Thr Leu
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic Mart1/MelanA-analogue peptide (AA 26-
      35)

<400> SEQUENCE: 2

Glu Leu Ala Gly Ile Gly Ile Leu Thr Val
1               5                   10

```
<210> SEQ ID NO 3
<211> LENGTH: 10
<212> TYPE: PRT
<213> ORGANISM: Influenza virus

<400> SEQUENCE: 3

Lys Leu Gly Glu Phe Tyr Asn Gln Met Met
1               5                   10

<210> SEQ ID NO 4
<211> LENGTH: 9
<212> TYPE: PRT
<213> ORGANISM: Homo sapiens

<400> SEQUENCE: 4

Phe Leu Trp Gly Pro Arg Ala Leu Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic gp100-analogue peptide, AA 209-217

<400> SEQUENCE: 5

Ile Met Asp Gln Val Pro Phe Ser Val
1               5

<210> SEQ ID NO 6
<211> LENGTH: 9
<212> TYPE: PRT
<213> ORGANISM: Homo sapiens

<400> SEQUENCE: 6

Tyr Met Asp Gly Thr Met Ser Gln Val
1               5

<210> SEQ ID NO 7
<211> LENGTH: 10
<212> TYPE: PRT
<213> ORGANISM: Homo sapiens

<400> SEQUENCE: 7

Val Leu Pro Asp Val Phe Ile Arg Cys Val
1               5                   10

<210> SEQ ID NO 8
<211> LENGTH: 9
<212> TYPE: PRT
<213> ORGANISM: Homo sapiens

<400> SEQUENCE: 8

Gly Leu Tyr Asp Gly Met Glu His Leu
1               5

<210> SEQ ID NO 9
<211> LENGTH: 10
<212> TYPE: PRT
<213> ORGANISM: Homo sapiens

<400> SEQUENCE: 9

Gly Val Tyr Asp Gly Arg Glu His Thr Val
1               5                   10
```

```
<210> SEQ ID NO 10
<211> LENGTH: 9
<212> TYPE: PRT
<213> ORGANISM: Influenza virus

<400> SEQUENCE: 10

Cys Thr Glu Leu Lys Leu Ser Asp Tyr
1               5

<210> SEQ ID NO 11
<211> LENGTH: 9
<212> TYPE: PRT
<213> ORGANISM: Influenza virus

<400> SEQUENCE: 11

Val Ser Asp Gly Gly Pro Asn Leu Tyr
1               5

<210> SEQ ID NO 12
<211> LENGTH: 9
<212> TYPE: PRT
<213> ORGANISM: Homo sapiens

<400> SEQUENCE: 12

Glu Val Asp Pro Ile Gly His Leu Tyr
1               5

<210> SEQ ID NO 13
<211> LENGTH: 9
<212> TYPE: PRT
<213> ORGANISM: Homo sapiens

<400> SEQUENCE: 13

Glu Ala Asp Pro Thr Gly His Ser Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic tyrosinase analogue peptide, AA 243-
      25

<400> SEQUENCE: 14

Lys Ser Asp Ile Cys Thr Asp Glu Tyr
1               5

<210> SEQ ID NO 15
<211> LENGTH: 9
<212> TYPE: PRT
<213> ORGANISM: Influenza virus

<400> SEQUENCE: 15

Ile Leu Arg Gly Ser Val Ala His Lys
1               5

<210> SEQ ID NO 16
<211> LENGTH: 9
<212> TYPE: PRT
<213> ORGANISM: Homo sapiens

<400> SEQUENCE: 16

Ser Leu Phe Arg Ala Val Ile Thr Lys
1               5
```

```
<210> SEQ ID NO 17
<211> LENGTH: 9
<212> TYPE: PRT
<213> ORGANISM: Homo sapiens

<400> SEQUENCE: 17

Leu Ile Tyr Arg Arg Arg Leu Met Lys
1               5

<210> SEQ ID NO 18
<211> LENGTH: 9
<212> TYPE: PRT
<213> ORGANISM: Homo sapiens

<400> SEQUENCE: 18

Ala Phe Leu Pro Trp His Arg Leu Phe
1               5

<210> SEQ ID NO 19
<211> LENGTH: 9
<212> TYPE: PRT
<213> ORGANISM: Homo sapiens

<400> SEQUENCE: 19

Asn Tyr Lys His Cys Phe Pro Glu Ile
1               5

<210> SEQ ID NO 20
<211> LENGTH: 9
<212> TYPE: PRT
<213> ORGANISM: Homo sapiens

<400> SEQUENCE: 20

Val Tyr Phe Phe Leu Pro Asp His Leu
1               5

<210> SEQ ID NO 21
<211> LENGTH: 9
<212> TYPE: PRT
<213> ORGANISM: Homo sapiens

<400> SEQUENCE: 21

Ile Met Pro Lys Ala Gly Leu Leu Ile
1               5

<210> SEQ ID NO 22
<211> LENGTH: 9
<212> TYPE: PRT
<213> ORGANISM: Homo sapiens

<400> SEQUENCE: 22

Ser Glu Ile Trp Arg Asp Ile Asp Phe
1               5

<210> SEQ ID NO 23
<211> LENGTH: 10
<212> TYPE: PRT
<213> ORGANISM: Homo sapiens

<400> SEQUENCE: 23

Met Glu Val Asp Pro Ile Gly His Leu Tyr
1               5                   10

<210> SEQ ID NO 24
<211> LENGTH: 13
<212> TYPE: PRT
```

```
<213> ORGANISM: Artificial Sequence
<220> FEATURE:
<223> OTHER INFORMATION: Synthetic tyrosinase analogue peptide, AA 450-
      46

<400> SEQUENCE: 24

Ser Tyr Leu Gln Asp Ser Val Pro Asp Ser Phe Gln Asp
1               5                   10

<210> SEQ ID NO 25
<211> LENGTH: 16
<212> TYPE: PRT
<213> ORGANISM: Homo sapiens

<400> SEQUENCE: 25

Trp Asn Arg Gln Leu Tyr Pro Glu Trp Thr Glu Ala Gln Arg Leu Asp
1               5                   10                  15

<210> SEQ ID NO 26
<211> LENGTH: 14
<212> TYPE: PRT
<213> ORGANISM: Homo sapiens

<400> SEQUENCE: 26

Leu Leu Lys Tyr Arg Ala Arg Glu Pro Val Thr Lys Ala Glu
1               5                   10

<210> SEQ ID NO 27
<211> LENGTH: 16
<212> TYPE: PRT
<213> ORGANISM: Homo sapiens

<400> SEQUENCE: 27

Lys Lys Leu Leu Thr Gln His Phe Val Gln Glu Asn Tyr Leu Glu Tyr
1               5                   10                  15
```